(12) United States Patent
Lennon

(10) Patent No.: US 7,094,842 B2
(45) Date of Patent: Aug. 22, 2006

(54) COMPOSITION CONTAINING A SILICONE COPOLYMER AND AN AMPS-LIKE POLYMER AND/OR ORGANIC POWDER

(75) Inventor: Paula Lennon, Lyons (FR)

(73) Assignee: L'Oreal, Paris (FR)

( * ) Notice: Subject to any disclaimer, the term of this patent is extended or adjusted under 35 U.S.C. 154(b) by 423 days.

(21) Appl. No.: 10/334,979

(22) Filed: Jan. 2, 2003

(65) Prior Publication Data

US 2003/0171479 A1    Sep. 11, 2003

Related U.S. Application Data

(60) Provisional application No. 60/356,143, filed on Feb. 14, 2002, provisional application No. 60/356,177, filed on Feb. 14, 2002, provisional application No. 60/356,142, filed on Feb. 14, 2002, provisional application No. 60/355,823, filed on Feb. 13, 2002.

(30) Foreign Application Priority Data

| Jan. 4, 2002 | (FR) | 02 00095 |
| Jan. 4, 2002 | (FR) | 02 00096 |
| Jan. 4, 2002 | (FR) | 02 00097 |
| Jan. 4, 2002 | (FR) | 02 00099 |

(51) Int. Cl.
   *C08G 283/12*    (2006.01)
(52) U.S. Cl. ............ 525/479; 525/55; 524/28.4; 424/70.1; 528/31; 528/32; 516/55
(58) Field of Classification Search ........... 525/479, 525/55; 524/284, 28.4; 424/70.1; 528/31, 528/32; 516/55
   See application file for complete search history.

(56) References Cited

U.S. PATENT DOCUMENTS

| 4,652,445 A | * | 3/1987 | Ort | 424/70.14 |
| 5,965,115 A | | 10/1999 | Bolich, Jr. et al. | |
| 6,013,682 A | * | 1/2000 | Dalle et al. | 516/55 |
| 6,194,452 B1 | * | 2/2001 | Murad | 514/474 |
| 6,399,081 B1 | | 6/2002 | Nakanishi et al. | |
| 2001/0041768 A1 | | 11/2001 | Lorant | |

FOREIGN PATENT DOCUMENTS

| EP | 0 380 428 A1 | 8/1990 |
| EP | 0 410 899 A1 | 1/1991 |
| EP | 0 417 866 A1 | 3/1991 |
| EP | 0 745 370 A1 | 12/1996 |
| EP | 0 755 674 A1 | 1/1997 |
| EP | 0 832 637 A1 | 4/1998 |
| EP | 0 869 142 A2 | 10/1998 |
| EP | 0 958 805 A2 | 11/1999 |
| EP | 1 010 715 A1 | 6/2000 |
| EP | 1 023 893 A1 | 8/2000 |
| EP | 1 064 930 A1 | 1/2001 |
| EP | 1 097 703 A1 | 5/2001 |
| WO | WO 93 14180 A | 7/1993 |
| WO | 97/32560 | * 9/1997 |
| WO | WO 98 00103 | 1/1998 |
| WO | WO 98 56890 | 12/1998 |
| WO | WO 99 24011 | 5/1999 |
| WO | WO 00 42152 | 7/2000 |
| WO | WO 01 14458 A1 | 3/2001 |
| WO | WO 02 03932 A2 | 1/2002 |

* cited by examiner

*Primary Examiner*—Kuo-Liang Peng
(74) *Attorney, Agent, or Firm*—Oblon, Spivak, McClelland, Maier & Neustadt, P.C.

(57) ABSTRACT

A composition containing, in a physiologically acceptable medium, (1) at least one aqueous phase containing particles of a substantially linear block silicone copolymer, and (2) at least one polymer containing at least one monomer having an ethylenic unsaturation and a sulphonic group, and/or at least on organic powder.

42 Claims, No Drawings

US 7,094,842 B2

COMPOSITION CONTAINING A SILICONE COPOLYMER AND AN AMPS-LIKE POLYMER AND/OR ORGANIC POWDER

FIELD OF THE INVENTION

The present invention relates to a composition comprising (1) an aqueous phase comprising an aqueous dispersion of particles of a substantially linear block silicone copolymer; and (2) at least one compound selected from the group consisting of a polymer comprising at least one monomer having an ethylenic unsaturation and a sulphonic group, at least one organic powder, and mixtures thereof, and to the use of such compositions in the cosmetic and dermatological fields, in particular for the care, treatment and cleansing of and/or for the application of makeup to the skin of the body or of the face, the hair and/or the lips.

BACKGROUND OF THE INVENTION

To provide a moisturizing effect and an emollient effect, current cosmetic compositions are most often provided in the form of an emulsion containing an aqueous phase and an oily phase. Depending on the direction of the dispersion, it may be an oil-in-water (O/W) type emulsion consisting of an aqueous dispersing continuous phase and an oily dispersed discontinuous phase, or a water-in-oil (W/O) type emulsion consisting of an oily dispersing continuous phase and an aqueous dispersed discontinuous phase. O/W emulsions are the most in demand in the cosmetic field because they contain, as external phase, an aqueous phase which confers on them, during application to the skin, a fresher, less greasy and lighter feel than W/O emulsions.

However, the feel of cosmetic compositions and in particular of these emulsions may be unsatisfactory because they often lack smoothness during application. To overcome this disadvantage, texturing agents may be added which confer smoothness to the composition containing them. For example, EP-A-874017 describes particles of block silicone copolymer in the form of silicone-in-water dispersions, which are appropriate for incorporation into care products and providing smoothness thereto.

However, while the incorporation of such a dispersion indeed provides smoothness, it also provides a sticky effect during application to the skin, which is unpleasant for the user.

The objective of the present invention is to enable production of emulsions having good cosmetic properties without having the disadvantages of the prior art.

SUMMARY OF THE INVENTION

It has been discovered unexpectedly that the use of a polymer containing at least one monomer having an ethylenic unsaturation and a sulphonic group, preferably a polymer or copolymer of 2-acrylamido-2-methylpropanesulphonic acid (AMPS), and/or of at least one organic powder in a composition containing particles in emulsion as described, for example, in EP-A-874017 makes it possible to reduce the sticky effect associated with application of such emulsions while retaining the smoothness effect, and makes it possible to produce cosmetic compositions, in particular emulsions (particularly oil-in-water emulsions), having very good cosmetic properties.

DETAILED DESCRIPTION OF THE INVENTION

According to the present invention, a composition comprising, in a physiologically acceptable medium, (1) at least one aqueous phase comprising, in dispersion, particles of a substantially linear block silicone copolymer; (2) and at least one compound selected from the group consisting of a polymer containing at least one monomer having an ethylenic unsaturation and a sulphonic group, at least one organic powder, and mixtures thereof is provided.

The composition of the present invention, being intended in particular for topical application, comprises a physiologically acceptable medium, that is, a medium compatible with keratin materials such as the skin, the nails, the mucous membranes, the hair and/or any other cutaneous zone of the body. The composition preferably is a cosmetic or dermatological composition.

In the present application, the expression "substantially linear copolymer" is understood to mean a copolymer containing few branches, and generally less than 2 mol % of siloxane units.

Moreover, the expression "particles" is understood to mean the block silicone copolymer globules which are in dispersion in water and form a silicone-in-water emulsion.

The composition obtained according to the invention has the advantage of having a homogeneous, very smooth, non-sticky and fresh texture upon application, which is therefore very pleasant to use.

In addition, it has been discovered that substantially linear block silicone copolymer particles in aqueous dispersion improve the dispersion of organic powders in compositions. Accordingly, another aspect of the present invention is the use of an aqueous dispersion of substantially linear block silicone copolymer particles to improve the dispersion of organic powders in a composition comprising at least one aqueous phase.

Furthermore, the dispersion of substantially linear silicone copolymer particles used in the compositions according to the present invention makes it possible to prepare compositions, preferably oil-in-water emulsions, which remain stable over time at room temperature or at higher temperatures, and to preserve these properties, regardless of the fluidity of the composition. It is thus possible to prepare both thick emulsions which are particularly effective for the treatment of dry skin and very fluid emulsions. The viscosity of such emulsions may vary to a large extent and range, for example, from 0.05 Pa.s to 20 Pa.s, preferably from 0.05 to 10 Pa.s, these viscosities being measured at about 25° C. using a "Rheomat 180" viscometer which is in general equipped with a No. 2 rotor for viscosity ranges from 0.02 Pa.s to 0.7 Pa.s, with a No. 3 rotor for viscosity ranges from 0.2 Pa.s to 4 Pa.s, and with a No. 4 rotor for viscosity ranges from 2 Pa.s to 23 Pa.s.

Moreover, the compositions according to the present invention make it possible to obtain stable compositions containing oxidation-sensitive hydrophilic active agents which tend not only to become destabilized themselves but also tend to destabilize the compositions containing them, particularly emulsions. The dispersion of particles of block copolymer stabilizes both oxidation-sensitive hydrophilic active agents and the compositions containing such active agents.

Block Silicone Copolymer Particles

The silicone copolymer constituting the globules or particles in dispersion in the aqueous phase is a substantially linear block copolymer, that is, a non-crosslinked copolymer, obtained by chain extension and not by crosslinking.

The aqueous dispersion of particles of block copolymer is a silicone-in-water emulsion (Sil/W) wherein the oily globules are constituted from a silicone of high viscosity, so that these globules seem to form as "soft particles".

The compositions may comprise dispersions of one or more types of substantially linear block silicone copolymer. The block silicone copolymers are present in the composition of the invention in concentrations, as active material, which may vary widely depending on the other ingredients of the composition and the desired aim. The concentration, as active material (A.M.), of block silicone copolymer preferably ranges from 0.01 to 15% by weight, more preferably from 0.1 to 10%, and most preferably from 0.5 to 5% by weight relative to the total weight of the composition.

The size of the block silicone copolymer particles may vary widely. Preferably, the silicone copolymer particles generally have a number-average size of less than or equal to 2 microns, more preferably of less than or equal to 1 micron.

The aqueous dispersions of substantially linear block silicone copolymer particles used according to the invention are preferably those described in EP-A-874017, the entire disclosure of which is hereby incorporated by reference. According to EP-A-874017, the silicone copolymers constituting these particles can be obtained by chain extension reaction, in the presence of a catalyst, from at least:

(a) one polysiloxane (i) having at least one reactive group and preferably one or two reactive groups per molecule; and
(b) one organosilicone compound (ii) which reacts with the polysiloxane (i) by chain extension reaction.

The polysiloxane (i) is preferably chosen from the compounds of formula (I):

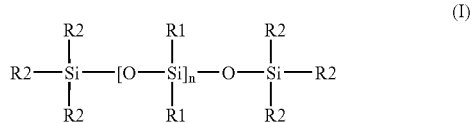

in which $R_1$ and $R_2$, independently of each other, represent a hydrocarbon group having from 1 to 20 carbon atoms, preferably from 1 to 10 carbon atoms, such as methyl, ethyl, propyl or butyl, or an aryl group such as phenyl, or a reactive group, n is an integer greater than 1, provided that there is on average between one and two reactive groups per polymer.

The expression "reactive group" is understood to mean any group capable of reacting with the organo-silicone compound (ii) to form a block copolymer. Suitable reactive groups include, for example, hydrogen; aliphatically unsaturated groups, preferably vinyl, allyl or hexanyl groups; the hydroxyl group; alkoxy groups such as methoxy, ethoxy or propoxy; alkoxyalkoxy groups; the acetoxy group; amino groups, and mixtures thereof. Preferably, more than 90%, and more preferably more than 98%, of reactive groups are at the chain end, that is, the radicals $R_2$ generally constitute more than 90%, more preferably more than 98%, of the reactive groups.

Preferably, n is such that the polysiloxanes have a viscosity ranging from about 1 to $1 \times 10^6$ mm$^2$/sec at 25° C. n may be, for example, an integer ranging from about 5 to 30, preferably from 10 to 30, more preferably from 15 to 25.

The polysiloxanes of formula (I) are preferably substantially linear polymers, that is, polymers containing few branches, and generally less than 2 mol % of the siloxane units. Moreover, the groups $R_1$ and $R_2$ may be optionally substituted with amino groups, epoxy groups, groups containing sulphur, silicon or oxygen.

Preferably, at least 80% of the groups $R_1$ are alkyl groups. Methyl groups are most preferred.

Preferably, the reactive group $R_2$ at the chain end is an aliphatically unsaturated. Vinyl groups are most preferred.

Preferred polysiloxanes (i) include, for example, dimethylvinylsiloxypolydimethylsiloxane, a compound of formula (I) in which the radicals $R_1$ are methyl radicals, and, at the chain end, the radical $R_2$ is a vinyl radical while the other two radicals $R_2$ are methyl radicals.

The organosilicone compound (ii) is preferably chosen from the polysiloxanes of formula (I) or compounds acting as chain extension agents. If it is a compound of formula (I), the polysiloxane (i) preferably contains a first reactive group and the organosilicone compound (ii) preferably contains a second reactive group which reacts with the first. If it is a chain extension agent, the compound is preferably a silane, a siloxane (disiloxane or trisiloxane) or a silazane. Preferably, the organosilicone compound (ii) is a liquid organohydrogenpolysiloxane of formula (II):

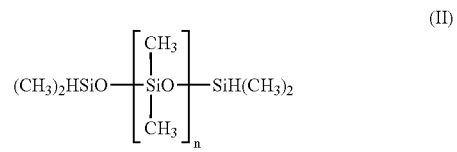

where n is an integer greater than 1, preferably greater than 10 (for example, ranging from 5 to 30, preferably from 10 to 30, and more preferably from 15 to 25. According to a particularly preferred embodiment of the invention, n is equal to 20.

The block silicone copolymers used according to the invention are preferably free from oxyalkylenated groups, especially oxyethylenated and/or oxypropylenated groups.

The catalyst of the reaction between the polysiloxane and the organosilicone compound is preferably chosen from metals, preferably from platinum, rhodium, tin, titanium, copper and lead. The catalyst is most preferably platinum or rhodium.

The dispersion of silicone copolymer particles used according to the invention is preferably obtained, for example, by mixing (a) water, (b) at least one emulsifier, (c) the polysiloxane (i), (d) the organosilicone compound (ii) and (e) a catalyst. Preferably, one of the constituents (c), (d) or (e) is added last to the mixture so that the chain extension reaction only starts in the dispersion.

Emulsifiers which may be used in the method of preparation described above for obtaining the aqueous dispersion of particles include, for example, non-ionic or ionic (anionic, cationic or amphoteric) emulsifiers. They are preferably non-ionic emulsifiers which may be chosen from polyalkylene glycol ethers of a fatty alcohol, containing from 8 to 30 carbon atoms, preferably from 10 to 22 carbon atoms; polyoxyalkylenated, preferably polyoxyethylenated, alkyl esters of sorbitan, where the alkyl radical contains from 8 to 30 carbon atoms, preferably from 10 to 22 carbon atoms; polyoxyalkylenated, preferably polyoxyethylenated, alkyl esters, where the alkyl radical contains from 8 to 30 carbon atoms, preferably from 10 to 22 carbon atoms; polyethylene glycols; polypropylene glycols; diethylene glycols; and mixtures thereof. The quantity of emulsifier(s) present is preferably from 1 to 30% by weight relative to the total weight of the reaction mixture.

The emulsifier used to obtain the aqueous dispersion of particles is preferably chosen from polyethylene glycol ethers of fatty alcohols and mixtures thereof, particularly polyethylene glycol ethers of alcohols containing 12 or 13 carbon atoms or from 2 to 100 oxyethylenated units, preferably from 3 to 50 oxyethylenated units, and mixtures thereof, such as, for example, $C_{12}$–$C_{13}$ Pareth-3, $C_{12}$–$C_{13}$ Pareth-23 and mixtures thereof.

According to a particularly preferred embodiment of the invention, the dispersion of particles of silicone copolymer is obtained from dimethylvinylsiloxypolydimethylsiloxane (or divinyldimethicone) as compound (i), and from the compound of formula (II) where n=20, as compound (ii), preferably in the presence of a platinum-type catalyst, and the dispersion of particles is preferably obtained in the presence of $C_{12}$–$C_{13}$ Pareth-3 and $C_{12}$–$C_{13}$ Pareth-23 as emulsifiers.

A preferred example of dispersion of particles of silicone copolymer is the product marketed under the name HMW 2220 by the company Dow Corning (CTFA name: divinyldimethicone/dimethicone copolymer/$C_{12}$–$C_{13}$ Pareth-3/$C_{12}$–$C_{13}$ Pareth-23), which is a 60% aqueous dispersion of divinyldimethicone/dimethicone copolymer containing $C_{12}$–$C_{13}$ Pareth-3 and $C_{12}$–$C_{13}$ Pareth-23, the said dispersion comprising about 60% by weight of copolymer; 2.8% by weight of $C_{12}$–$C_{13}$ Pareth-23; 2% by weight of $C_{12}$–$C_{13}$ Pareth-3; 0.31% by weight of preservatives, the remainder up to 100% being water.

Polymers Containing at Least One Monomer Having an Ethylenic Unsaturation and a Sulphonic Group The polymers used in accordance with the invention are preferably homopolymers or copolymers containing at least one monomer having an ethylenic unsaturation and a sulphonic group, which may be in free form or partially or completely neutralized. These polymers may optionally comprise at least one hydrophobic part. Also, these polymers may be amphiphilic polymers.

Preferably, the polymers in accordance with the invention are partially or completely neutralized with an inorganic base (for example, sodium hydroxide, potassium hydroxide, aqueous ammonia) or an organic base such as, for example, mono-, di- or triethanolamine, an aminomethylpropanediol, N-methylglucamine, basic amino acids such as arginine and lysine, and mixtures of these compounds. They are preferably neutralized. The expression "neutralized" is understood in the present invention to mean completely or practically completely neutralized polymers, that is, at least 90% neutralized.

The polymers used in the composition of the invention preferably have a number-average molecular weight ranging from 1,000 to 20,000,000 g/mol, more preferably ranging from 20,000 to 5,000,000 and most preferably from 100,000 to 1,500,000 g/mol.

These polymers according to the invention may be crosslinked or non-crosslinked. Preferably, the polymers are crosslinked.

The monomers having an ethylenic unsaturation and a sulphonic group of the polymer used in the composition of the invention are preferably vinylsulphonic acid, styrenesulphonic acid, (meth)acrylamido($C_1$–$C_{22}$)alkylsulphonic acids, N-($C_1$–$C_{22}$) alkyl (meth) acrylamido ($C_1$–$C_{22}$) alkylsulphonic acids such as undecylacrylamidomethanesulphonic acid and the partially or completely neutralized forms thereof, and mixtures thereof.

According to a preferred embodiment of the invention, monomers having an ethylenic unsaturation and a sulphonic group are used. For example, (meth)acrylamido($C_1$–$C_{22}$) alkylsulphonic acids such as, for example, acrylamidomethanesulphonic acid, acrylamidoethanesulphonic acid, acrylamidopropanesulphonic acid, 2-acrylamido-2-methylpropanesulphonic acid, 2-methacrylamido-2-methylpropanesulphonic acid, 2-acrylamido-n-butanesulphonic acid, 2-acrylamido-2,4,4-trimethylpentanesulphonic acid, 2-methacrylamidododecylsulphonic acid, 2-acrylamido-2,6-dimethyl-3-heptanesulphonic acid, and the partially or completely neutralized forms thereof, and mixtures thereof are used.

Most preferably, 2-acrylamido-2-methylpropanesulphonic acid (AMPS) and the partially or completely neutralized forms thereof are used.

When the polymers are crosslinked, the crosslinking agents may be chosen from the olefinically polyunsaturated compounds commonly used for the crosslinking of polymers obtained by free-radical polymerization.

Suitable examples of such crosslinking agents include divinylbenzene, diallyl ether, dipropylene glycol diallyl ether, polyglycol diallyl ethers, triethylene glycol divinyl ether, hydroquinone diallyl ether, ethylene glycol or tetraethylene glycol di(meth)acrylate, trimethylolpropane triacrylate, methylenebisacrylamide, methylenebismethacrylamide, triallylamine, triallyl cyanurate, diallyl maleate, tetraallylethylenediamine, tetraallyloxyethane, trimethylolpropane diallyl ether, allyl (meth)acrylate, allyl ethers of alcohols of the sugar series, or other allyl or vinyl ethers of polyfunctional alcohols, and the allyl esters of phosphoric and/or vinylphosphonic acid derivatives, or mixtures of these compounds.

According to a preferred embodiment of the invention, the crosslinking agent is chosen from methylenebisacrylamide, allyl methacrylate or trimethylolpropane triacrylate (TMPTA). The degree of crosslinking preferably ranges from 0.01 to 10 mol %, more preferably from 0.2 to 2 mol % relative to the polymer.

When the polymers used are homopolymers, they preferably contain only monomers having an ethylenic unsaturation and a sulphonic group and, if they are crosslinked, one or more crosslinking agents.

These homopolymers are preferably crosslinked and neutralized, and they are preferably obtained according to the method of preparation comprising the following steps:

(a) the monomer, such as 2-acrylamido-2-methylpropanesulphonic acid in free form, is dispersed or dissolved in a solution of tert-butanol or of water and tert-butanol;

(b) the solution or the dispersion of monomer obtained in (a) is neutralized with one or more inorganic or organic bases, preferably aqueous ammonia $NH_3$, in a quantity which makes it possible to obtain a degree of neutralization of the sulphonic acid functional groups of the polymer ranging from 90 to 100%;

(c) the crosslinking monomer(s) is(are) added to the solution or dispersion obtained in (b);

(d) conventional free-radical polymerization is carried out in the presence of initiators of free radicals at a temperature ranging from 10 to 150° C., the polymer precipitating from the tert-butanol-based solution or dispersion.

Suitable polymers of this type include, for example, crosslinked and neutralized homopolymers of 2-acrylamido-2-methylpropanesulphonic acid, marketed by the company Hoechst under the trade name "Hostacerin AMPS" (CTFA name: ammonium polyacryldimethyltauramide).

The polymer may also be an amphiphilic homopolymer chosen from random amphiphilic polymers of AMPS modified by reaction with a $C_6$–$C_{22}$ mono-n-alkylamine or di-n-alkylamine. For example, suitable homopolymers of this type include those described in patent application WO-A-00/31154, which are graft homopolymers.

When the polymers used are copolymers, they are preferably obtained from monomers having an ethylenic unsaturation and a sulphonic group and other monomers having an ethylenic unsaturation, that is, monomers having an ethylenic unsaturation without a sulphonic group.

The monomers having an ethylenic unsaturation and a sulphonic group are chosen from those described above.

The monomers having an ethylenic unsaturation without a sulphonic group may be chosen from hydrophilic monomers, hydrophobic monomers and mixtures thereof. When the polymer contains hydrophobic monomers, it constitutes an amphiphilic polymer.

Suitable hydrophilic monomers having an ethylenic unsaturation include, for example,(meth)acrylic acids, their β-substituted alkyl derivatives or their esters obtained with monoalcohols or mono- or polyalkylene glycols, (meth) acrylamides, vinylpyrrolidone, vinylformamide, maleic anhydride, itaconic acid or maleic acid or mixtures of these compounds.

Suitable copolymers obtained from monomers having an ethylenic unsaturation and a sulphonic group and hydrophilic monomers having an ethylenic unsaturation include, for example, those obtained from AMPS and acrylamide or methylacrylamide, such as for example the acrylamide/ sodium acrylamido-2-methylpropanesulphonate copolymer in inverse emulsion at 40% in polysorbate, marketed under the name SIMULGEL 600 by the company SEPPIC. Suitable copolymers also include, for example, copolymers of AMPS and vinylpyrrolidone or of vinylformamide, such as the products marketed under the name ARISTOFLEX AVC by the company CLARIANT.

When the monomers having an ethylenic unsaturation and a sulphonic group are copolymerized with ethylenically unsaturated hydrophobic monomers containing a fatty chain, the polymer obtained is amphiphilic, that is, it contains both a hydrophilic part and a hydrophobic part.

The amphiphilic polymers may contain, in addition, one or more ethylenically unsaturated monomers containing no fatty chain, such as (meth)acrylic acids, their β-substituted alkyl derivatives or their esters obtained with monoalcohols or mono- or polyalkylene glycols, (meth)acrylamides, vinylpyrrolidone, vinylformamide, maleic anhydride, itaconic acid or maleic acid or mixtures of these compounds.

Suitable amphiphilic polymers include, for example, those obtained from AMPS and from at least one ethylenically unsaturated hydrophobic monomer containing at least one hydrophobic part having from 6 to 50 carbon atoms, preferably from 6 to 22 carbon atoms, more preferably from 6 to 18 carbon atoms and most particularly 12 to 18 carbon atoms.

Examples of these copolymers are described in particular in patent application EP-A-750899, U.S. Pat. No. 5,089,578 and in the following publications by Yotaro Morishima:

"Self-assembling amphiphilic polyelectrolytes and their nanostructures—Chinese Journal of Polymer Science Vol. 18, No. 40, (2000), 323–336";

"Miscelle formation of random copolymers of sodium 2-(acrylamido)-2-methylpropanesulfonate and a nonionic surfactant macromonomer in water as studied by fluorescence and dynamic light scattering—Macromolecules 2000, Vol. 33, No. 10-3694–3704";

"Solution properties of miscelle networks formed by nonionic moieties covalently bound to a polyelectrolyte: salt effects on Theological behavior—Langmuir, 2000, Vol. 16, No. 12, 5324–5332";

"Stimuli responsive amphiphilic copolymers of sodium 2-(acrylamido)-2-methylpropanesulfonate and associative macromonomers—Polym. Preprint, Div. Polym. Chem. 1999, 40(2), 220–221".

The ethylenically unsaturated hydrophobic monomers of these particular copolymers are preferably chosen from acrylates, alkylacrylates, acrylamides and alkylacrylamides of the following formula (III):

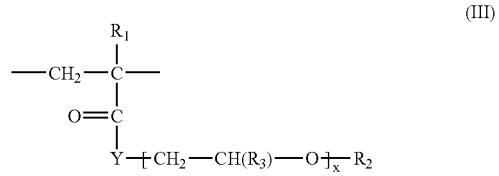

in which $R_1$ and $R_3$, which are identical or different, denote a hydrogen atom or a substantially linear or branched $C_1$–$C_6$ alkyl radical (preferably methyl); Y denotes O or NH; $R_2$ denotes a hydrophobic hydrocarbon radical containing at least from 6 to 50 carbon atoms, preferably from 6 to 22 carbon atoms, more preferably from 6 to 18 carbon atoms and most preferably from 12 to 18 carbon atoms; x denotes a number of moles of alkylene oxide and preferably varies from 0 to 100.

The radical $R_2$ is preferably chosen from substantially linear $C_6$–$C_{18}$ alkyl radicals (for example n-hexyl, n-octyl, n-decyl, n-hexadecyl, n-dodecyl, n-octadecyl) or branched or cyclic $C_6$–$C_{18}$ alkyl radicals (for example cyclododecane ($C_{12}$) or adamantane ($C_{10}$)); perfluorinated $C_6$–$C_{18}$ alkyl radicals (for example the group of formula —$(CH_2)_2$—$(CF_2)_9$—$CF_3$); the cholesteryl radical ($C_{27}$) or a cholesterol ester residue such as the cholesteryl oxyhexanoate group; polycyclic aromatic groups such as naphthalene or pyrene. Among these radicals, the most preferred are the substantially linear alkyl radicals, preferably the n-dodecyl, n-hexadecyl or n-octadecyl radical, and mixtures thereof.

According to a particularly preferred embodiment of the invention, the monomer of formula (III) contains at least one alkylene oxide unit (x≧1), preferably several alkylene oxide units (x>1) constituting a polyoxyalkylenated chain. The polyoxyalkylenated chain preferably consists of ethylene oxide units and/or propylene oxide units, more preferably consists of ethylene oxide units. The number of oxyalkylenated units (or number of moles of alkylene oxide) preferably varies from 3 to 100, more preferably from 3 to 50 and most preferably from 7 to 25.

Suitable polymers include, for example, crosslinked or non-crosslinked and neutralized or nonneutralized copolymers containing from 15 to 60% by weight of AMPS units and from 40 to 85% by weight of ($C_8$–$C_{16}$) alkyl(meth)acrylamide units or ($C_8$–$C_{16}$)alkyl(meth)acrylate units, relative to the polymer, such as those described in application EP-A-750 899;

terpolymers containing from 10 to 90 mol % of acrylamide units, from 0.1 to 10 mol % of AMPS units and from 5 to 80 mol % of n-($C_6$–$C_{18}$)alkylacrylamide units, relative to the polymer, such as those described in U.S. Pat. No. 5,089,578.

Suitable amphiphilic polymers include, for example, copolymers of completely neutralized AMPS and of n-dodecyl, n-hexadecyl and/or n-octadecyl methacrylate, and copolymers of AMPS and of n-dodecyl-methacrylamide, which are non-crosslinked and crosslinked, such as those described in the articles by Morishima cited above.

Preferably, the copolymers consist of 2-acrylamido-2-methylpropanesulphonic acid (AMPS) units of the following formula (IV):

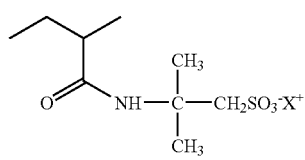

(IV)

in which $X^+$ is a proton, an alkali metal cation, an alkaline-earth metal cation or the ammonium ion, and of units of the following formula (V):

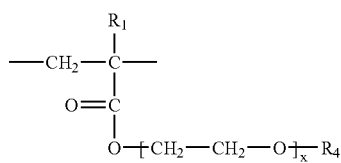

(V)

in which x denotes an integer ranging from 3 to 100, preferably from 3 to 50, more preferably from 7 to 25; $R_1$ has the same meaning as that indicated above in formula (I) and $R_4$ denotes a substantially linear or branched $C_6$–$C_{22}$, more preferably $C_{10}$–$C_{22}$, alkyl.

The particularly preferred amphiphilic polymers of this type are those for which x=25, $R_1$ denotes methyl and $R_4$ represents n-dodecyl; they are described in the articles by Morishima mentioned above. Other preferred polymers are those for which x=8 or 25, $R_1$ denotes methyl and $R_4$ represents n-hexadecyl ($C_{16}$), n-octadecyl ($C_{18}$) or n-dodecyl ($C_{12}$), or mixtures thereof.

The polymers for which $X^+$ denotes sodium or ammonium are most preferred.

The preferred amphiphilic polymers used in the composition in accordance with the invention may be obtained according to conventional free-radical polymerization methods in the presence of one or more initiators such as, for example, azobisisobutyronitrile (AIBN), azobisdimethylvaleronitrile, 2,2-azobis[2-amidinopropane] hydrochloride (ABAH), organic peroxides such as dilauryl peroxide, benzoyl peroxide, tert-butyl hydroperoxide, and the like, inorganic peroxidized compounds such as potassium or ammonium persulphate or $H_2O_2$, optionally in the presence of reducing agents.

These amphiphilic polymers are preferably obtained by free-radical polymerization in tert-butanol medium from which they precipitate. Using polymerization by precipitation from tert-butanol, it is possible to obtain a size distribution of the polymer particles which is particularly favourable.

The reaction may be carried out at a temperature of between 0 and 150° C., preferably between 10 and 100° C., either at atmospheric pressure, or under reduced pressure. It may also be carried out under an inert atmosphere, preferably under nitrogen.

According to this method, 2-acrylamido-2-methylpropanesulphonic acid (AMPS) or one of its sodium or ammonium salts can be polymerized with an ester of (meth)acrylic acid and of a $C_{10}$–$C_{18}$ alcohol oxyethylenated with 8 mol of ethylene oxide (GENAPOL® C-080 from the company CLARIANT), of a $C_{11}$ oxo alcohol oxyethylenated with 8 mol of ethylene oxide (GENAPOL® UD-080 from the company CLARIANT), of a $C_{11}$ oxo alcohol oxyethylenated with 7 mol of ethylene oxide (GENAPOL® UD-070 from the company CLARIANT), of a $C_{12}$–$C_{14}$ alcohol oxyethylenated with 7 mol of ethylene oxide (GENAPOL® LA-070 from the company CLARIANT), of a $C_{12}$–$C_{14}$ alcohol oxyethylenated with 9 mol of ethylene oxide (GENAPOL® LA-090 from the company CLARIANT), of a $C_{12}$–$C_{14}$ alcohol oxyethylenated with 11 mol of ethylene oxide (GENAPOL® LA-110 from the company CLARIANT), of a $C_{16}$–$C_{18}$ alcohol oxyethylenated with 8 mol of ethylene oxide (GENAPOL® T-080 from the company CLARIANT), of a $C_{16}$–$C_{18}$ alcohol oxyethylenated with 15 mol of ethylene oxide (GENAPOL® T-150 from the company CLARIANT), of a $C_{16}$–$C_{18}$ alcohol oxyethylenated with 11 mol of ethylene oxide (GENAPOL® T-110-from the company CLARIANT), of a $C_{16}$–$C_{18}$ alcohol oxyethylenated with 20 mol of ethylene oxide (GENAPOL® T-200 from the company CLARIANT), of a $C_{16}$–$C_{18}$ alcohol oxyethylenated with 25 mol of ethylene oxide (GENAPOL® T-250 from the company CLARIANT), of a $C_{18}$–$C_{22}$ alcohol oxyethylenated with 25 mol of ethylene oxide and/or of a $C_{16}$–$C_{18}$ iso-alcohol oxyethylenated with 25 mol of ethylene oxide.

The mol % concentration of the units of formula (II) and of the units of formula (III) in the polymers according to the invention vary according to the desired cosmetic application and the Theological properties sought for the formulation. It may vary between 0.1 and 99.9 mol %.

Preferably, for the most hydrophobic polymers, the molar proportion of units of formula (I) or (III) varies from 50.1 to 99.9%, more preferably from 70 to 95%, and most preferably from 80 to 90%.

Preferably, for the polymers which are not very hydrophobic, the molar proportion of units of formula (I) or (III) varies from 0.1 to 50%, more preferably from 5 to 25%, and most preferably from 10 to 20%.

The distribution of the monomers in the polymers of the invention may be, for example, alternating, block (including multiblock) or random.

The polymers containing at least one monomer having an ethylenic unsaturation and a sulphonic group, which are used in the composition in accordance with the invention, are preferably present in quantities, as active material, ranging from 0.01 to 20% by weight, more preferably from 0.1 to 10% by weight, still more preferably from 0.1 to 5% by weight and most preferably from 0.5 to 2% by weight relative to the total weight of the composition.

Organic Powder

Suitable organic powders (also called organic fillers) which may be used in the composition of the invention include, for example, polyamide particles, preferably NYLON 12 powder, such as the products marketed under the name ORGASOL by the company Atochem; polyethylene powders and beads such as those marketed under the name ACUMIST (Acumist B-6, Acumist B-12) by the company Allied and those marketed under the name MICROTHENE by the company Equistar; microspheres based on acrylic or methacrylic copolymers, such as those made of ethylene glycol dimethacrylate/lauryl methacrylate copolymer, which are sold by the company Dow Corning under the name POLYTRAP, or those made of methyl methacrylate/ethylene glycol dimethacrylate copolymer, which are marketed under the name Microspheres M305 by the company Matsumoto; polymethyl methacrylate microspheres marketed under the name MICROSPHERE M-100 and M305 by the company Matsumoto or under the name COVABEAD by the company Wackherr; ethylene-acrylate copolymer powders such as those marketed under the name FLOBEADS by the company Sumitomo Seika Chemicals; expanded powders such as hollow microspheres, preferably, the microspheres marketed under the name EXPANCEL by the company Kemanord Plast or under the name MICROPEARL F 80 ED by the company Matsumoto; powders of natural organic materials such as maize, wheat or rice starches, crosslinked or otherwise, such as powders made of starch which is crosslinked with octenyl succinate anhydride, which are marketed under the name DRY-FLO by the company National Starch; microbeads of silicone resin such as those marketed under the name TOSPEARL by the company Toshiba Silicone; and mixtures thereof.

The organic powder may be introduced into the composition after mixing the other constituents. For example, in the case of an emulsion, the organic powder may be introduced after preparation of the emulsion, or alternatively, if an oily phase is present, into the oily phase of the composition. The organic powder may also be introduced during the preparation of the emulsion, into the aqueous phase or into the oily phase.

The organic powders used in the composition in accordance with the invention are preferably present in quantities, as active material, ranging from 0.01 to 30% by weight, more preferably from 0.1 to 20% by weight, most preferably from 1 to 10% by weight relative to the total weight of the composition.

The compositions according to the invention may be provided in any galenic form conventionally used for topical application. Preferably, they are in the form of aqueous gels or of aqueous or aqueous-alcohol solutions. It may also, upon addition of a fatty or oily phase, be provided in the form of lotion- or serum-type dispersions, of emulsions having a liquid or semi-liquid consistency of the milk type, which are obtained by dispersing a fatty phase in an aqueous phase (O/W) or conversely (W/O), or of suspensions or emulsions of a soft, semi-solid or solid consistency of the cream or gel type, or alternatively of multiple emulsions (W/O/W or O/W/O), of microemulsions, of vesicular dispersions of the ionic and/or non-ionic type, or of wax/aqueous phase dispersions. These compositions are prepared according to the customary methods.

According to a preferred embodiment of the invention, the composition is provided in the form of an emulsion, most preferably an O/W emulsion.

In addition, the compositions according to the invention may be fluid to a greater or lesser degree and may have the appearance of a gel, a white or coloured cream, an ointment, a milk, a lotion, a serum, a paste or a mousse. They may be optionally applied to the skin in the form of an aerosol. They may also be provided in solid form, and for example in powdered form, or in cast form, in a dish or in the form of a stick.

The aqueous phase of the compositions according to the invention comprises at least water. It may consist of only the aqueous dispersion of the particles of block silicone copolymers or it may also comprise other water-soluble or water-dispersible constituents. In the anhydrous compositions, that is, compositions containing less than 5% by weight of water relative to the total weight of the composition, the aqueous phase preferably consists of only the aqueous dispersion of the particles of block silicone copolymers. According to the galenic form of the composition, the quantity of aqueous phase may range from 0.1 to 99% by weight, preferably from 0.5 to 98% by weight, more preferably from 30 to 95% by weight, and most preferably from 40 to 95% by weight relative to the total weight of the composition. The aqueous phase quantity depends on the galenic form of the composition desired. The quantity of water may represent all or part of the aqueous phase, and it is preferably at least 30% by weight relative to the total weight of the composition, particularly when the composition is provided in the form of an emulsion.

The compositions of the invention may contain, in the aqueous phase or in the oily phase if it contains an oily phase, one or more hydrophilic, lipophilic and/or amphiphilic organic solvents, which are physiologically acceptable, that is, which are well tolerated and which give a cosmetically acceptable feel.

The organic solvents, if present, preferably represent from 0.5 to 50%, more preferably from 2 to 20% of the total weight of the composition. The organic solvents are preferably chosen from the group consisting of hydrophilic organic solvents, lipophilic organic solvents, amphiphilic solvents, or mixtures thereof.

Suitable organic solvents include, for example, substantially linear or branched lower monoalcohols having from 1 to 8 carbon atoms, such as ethanol, propanol, butanol, isopropanol, isobutanol; polyols such as propylene glycol, isoprene glycol, butylene glycol, propylene glycol, glycerol, sorbitol; mono- or dialkyl isosorbide in which the alkyl groups have from 1 to 5 carbon atoms such as dimethyl isosorbide; polyethylene glycols, in particular those having from 6 to 80 ethylene oxides, such as polyethylene glycol 32 EO; ethylene glycol ethers such as diethylene glycol monomethyl or monoethyl ether; propylene glycol ethers such as dipropylene glycol methyl ether; polyol esters and ethers, such as esters of polypropylene glycol (PPG) and more especially esters of polypropylene glycol (PPG) and of a fatty acid, ethers of PPG and a fatty alcohol such as PPG-23 oleyl ether and PPG-36 oleate; fatty acid and alkyl esters, such as diisopropyl adipate, dioctyl adipate, alkyl benzoates; and mixtures thereof.

When the composition is in the form of an emulsion, the proportion of the oily phase of the emulsion may range, for example, from 5 to 80% by weight, preferably from 5 to 50% by weight, relative to the total weight of the composition. The oils, the emulsifiers and the coemulsifiers used in the composition in the form of an emulsion are chosen from those conventionally used in the cosmetic or dermatological field. The emulsifier and coemulsifier are preferably present in the composition in a proportion ranging from 0.3 to 30% by weight, preferably from 0.5 to 20% by weight relative to the total weight of the composition. The emulsion may, in addition, contain lipid vesicles.

The emulsions generally contain at least one emulsifier chosen from amphoteric, anionic, cationic or non-ionic emulsifiers, used alone or in the form of a mixture. The emulsifiers are appropriately chosen according to the emulsion to be obtained (W/O or O/W).

For the W/O emulsions, suitable emulsifiers include, for example, dimethicone copolyols such as the mixture of cyclomethicone and of dimethicone copolyol, sold under the name "DC 5225 C" by the company Dow Corning, and alkyldimethicone copolyols such as laurylmethicone copolyol sold under the name "Dow Corning 5200 Formulation Aid" by the company Dow Corning and cetyl dimethicone copolyol sold under the name ABIL EM $90^R$ by the company Goldschmidt, or the polyglyceryl-4 isostearate/cetyl dimethicone copolyol/hexyl laurate mixture sold under the name ABIL WE 09 by the company Goldschmidt. It is also possible to add thereto one or more coemulsifiers.

The coemulsifier, if present, is preferably chosen from the group comprising polyol alkyl esters. Suitable polyol alkyl esters include, for example, esters of glycerol and/or sorbitan like polyglycerol isostearate, such as the product marketed under the name Isolan GI 34 by the company Goldschmidt, sorbitan isostearate, such as the product marketed under the name Arlacel 987 by the company ICI, sorbitan and glycerol isostearate, such as the product marketed under the name Arlacel 986 by the company ICI, and mixtures thereof.

For the O/W emulsions, suitable emulsifiers include, for example, non-ionic surfactants, preferably esters of polyols and of a saturated or unsaturated chain fatty acid containing, for example, from 8 to 24 carbon atoms, preferably from 12 to 22 carbon atoms, and their oxyalkylenated derivatives, that is, derivatives containing oxyethylenated and/or oxypropylenated units, such as esters of glyceryl and of a $C_8$–$C_{24}$ fatty acid, and their oxyalkylenated derivatives; esters of polyethylene glycol and of a $C_8$–$C_{24}$ fatty acid, and their oxyalkylenated derivatives; esters of sorbitol and of a $C_8$–$C_{24}$ fatty acid, and their oxyalkylenated derivatives; esters of a sugar (sucrose, glucose, alkylglucose) and of a $C_8$–$C_{24}$ fatty acid, and their oxyalkylenated derivatives; fatty alcohol ethers; ethers of a sugar and of $C_8$–$C_{24}$ fatty alcohols, and mixtures thereof.

Suitable esters of glyceryl and of a fatty acid include, for example, glyceryl stearate (glyceryl mono-, di- and/or tristearate) (CTFA name: glyceryl stearate) or glyceryl ricinoleate, and mixtures thereof.

Suitable esters of polyethylene glycol and of a fatty acid include, for example, polyethylene glycol stearate (polyethylene glycol mono-, di- and/or tristearate), preferably polyethylene glycol monostearate 50 EO (CTFA name: PEG-50 stearate), polyethylene glycol monostearate 100 EO (CTFA name: PEG-100 stearate), and mixtures thereof.

It is also possible to use mixtures of these surfactants, such as for example the product containing glyceryl stearate and PEG-100 stearate, marketed under the name ARLACEL 165 by the company Uniquema, and the product containing glyceryl stearate (glyceryl mono- or distearate) and potassium stearate, marketed under the name TEGIN by the company Goldschmidt (CTFA name: glyceryl stearate SE).

Suitable esters of a fatty acid and of glucose or of alkylglucose include, for example, glucose palmitate, alkylglucose sesquistearates such as methylglucose sesquistearate, alkylglucose palmitates such as methylglucose or ethylglucose palmitate, fatty esters of methylglucoside and more especially the diester of methylglucoside and oleic acid (CTFA name: Methyl glucose dioleate); the mixed ester of methylglucoside and of the oleic acid/hydroxystearic acid mixture (CTFA name: Methyl glucose dioleate/hydroxystearate); the ester of methylglucoside and of isostearic acid (CTFA name: Methyl glucose isostearate); the ester of methylglucoside and of lauric acid (CTFA name: Methyl glucose laurate); the mixture of a monoester and of a diester of methylglucoside and of isostearic acid (CTFA name: Methyl glucose sesqui-isostearate); the mixture of a monoester and of a diester of methylglucoside and of stearic acid (CTFA name: Methyl glucose sesquistearate) and in particular the product marketed under the name Glucate SS by the company AMERCHOL, and mixtures thereof.

Suitable oxyethylenated ethers of a fatty acid and of glucose or of an alkylglucose include, for example, the oxyethylenated ethers of a fatty acid and of methylglucose, and in particular the polyethylene glycol ether of a diester of methyl glucose and of stearic acid containing about 20 mol of ethylene oxide (CTFA name: PEG-20 methyl glucose distearate) such as the product marketed under the name Glucam E-20 distearate by the company AMERCHOL; the polyethylene glycol ether of the mixture of a monoester and of a diester of methylglucose and of stearic acid containing about 20 mol of ethylene oxide (CTFA name: PEG-20 methyl glucose sesquistearate) and in particular the product marketed under the name Glucamate SSE-20 by the company AMERCHOL and that marketed under the name Grillocose PSE-20 by the company GOLDSCHMIDT, and mixtures thereof.

Suitable sucrose esters include, for example, sucrose palmitostearate, sucrose stearate and sucrose monolaurate.

Suitable fatty alcohol ethers include, for example, the ethers of polyethylene glycol and of a fatty alcohol containing from 8 to 30 carbon atoms, in particular from 10 to 22 carbon atoms, such as the ethers of polyethylene glycol and of cetyl alcohol, stearyl alcohol or cetearyl alcohol (mixture of cetyl and stearyl alcohols). There may be mentioned, for example, the ethers containing from 1 to 200, preferably from 2 to 100 oxyethylenated groups, such as those having the CTFA name Ceteareth-20, Ceteareth-30, and mixtures thereof.

Suitable sugar ethers include, for example, alkylpolyglucosides such as decylglucoside such as the product marketed under the name MYDOL 10 by the company Kao Chemicals, the product marketed under the name PLANTAREN 2000 by the company Henkel, and the product marketed under the name ORAMIX NS 10 by the company Seppic; caprylyl/capryl glucoside such as the product marketed under the name ORAMIX CG 110 by the company Seppic or under the name LUTENSOL GD 70 by the company BASF; laurylglucoside such as the products marketed under the names PLANTAREN 1200 N and PLANTACARE 1200 by the company Henkel; cocoglucoside such as the product marketed under the name PLANTACARE 818/UP by the company Henkel; cetostearyl glucoside optionally in the form of a mixture with cetostearyl alcohol, marketed for example under the name MONTANOV 68 by the company Seppic, under the name TEGO-CARE CG90 by the company Goldschmidt and under the name EMULGADE KE3302 by the company Henkel; arachidyl glucoside, for example in the form of the mixture of arachidyl and behenyl alcohols and of arachidyl glucoside marketed under the name MONTANOV 202 by the company Seppic; cocoyl-ethylglucoside, for example in the form of the mixture (35/65) with cetyl and stearyl alcohols, marketed under the name MONTANOV 82 by the company Seppic; and mixtures thereof.

When the composition is provided in the form of an emulsion, the nature of the oily phase of the emulsion is not critical. The oily phase may thus consist of all the fatty substances and in particular the oils conventionally used in the cosmetic or dermatological fields. The oily phase generally comprises at least one oil.

Suitable oils which may be used in the composition of the invention include, for example:

hydrocarbon oils of animal origin, such as perhydrosqualene;

hydrocarbon oils of plant origin, such as liquid triglycerides of fatty acids containing from 4 to 10 carbon atoms such as the triglycerides of heptanoic or octanoic acid or alternatively, for example, sunflower, maize, soyabean, gourd, grape seed, sesame, hazelnut, apricot, macadamia, arara, castor and avocado oils, the triglycerides of caprylic/capric acids such as those sold by the company Stearineries Dubois or those sold under the names Miglyol 810, 812 and 818 by the company Dynamit Nobel, jojoba oil, karite butter oil;

synthetic esters and ethers, in particular of fatty acids, such as the oils of formulae $R^aCOOR^b$ and $R^aOR^b$ in which $R^a$ represents the residue of a fatty acid containing from 8 to 29 carbon atoms, and $R^b$ represents a branched or unbranched hydrocarbon chain containing from 3 to 30 carbon atoms, such as for example purcellin oil, isononyl isononanoate, isopropyl myristate, 2-ethylhexyl palmitate, 2-octyldodecyl stearate, 2-octyldodecyl erucate, isostearyl isostearate; hydroxylated esters such as isostearyl lactate, octyl hydroxystearate, octyldodecyl hydroxystearate, diisostearyl malate, triisocetyl citrate, heptanoates, octanoates, decanoates of fatty alcohols; polyol esters, such as propylene glycol dioctanoate, neopentylglycol diheptanoate and diethylene glycol diisononanoate; and pentaerythritol esters such as pentaerythrityl tetraisostearate;

substantially linear or branched hydrocarbons, of inorganic or synthetic origin, such as volatile or non-volatile paraffin oils, and derivatives thereof, petroleum jelly, polydecenes, isohexadecane, isododecane, hydrogenated polyisobutene such as Parleam® oil;

fatty alcohols having from 8 to 26 carbon atoms, such as cetyl alcohol, stearyl alcohol and a mixture thereof (cetylstearyl alcohol), octyldodecanol, 2-butyloctanol, 2-hexyldecanol, 2-undecylpentadecanol, oleyl alcohol or linoleyl alcohol;

alkoxylated and in particular ethoxylated fatty alcohols such as oleth-12, ceteareth-12 and ceteareth-20;

partially hydrocarbon-based and/or silicone-based fluorinated oils such as those described in the document JP-A-2-295912. As fluorinated oils, there may also be mentioned perfluoromethylcyclopentane and perfluoro(1,3-dimethylcyclohexane), sold under the names "FLUTEC PC1®" and "FLUTEC PC3®" by the company BNFL Fluorochemicals; perfluoro(1,2-dimethylcyclobutane); perfluoroalkanes such as dodecafluoropentane and tetradecafluorohexane, sold under the names "PF 5050®" and "PF 5060®" by the company 3M, or alternatively bromoperfluorooctyl sold under the name "FORALKYL®" by the company Atochem; nonafluoromethoxybutane sold under the name "MSX 4518®" by the company 3M and nonafluoroethoxyisobutane; perfluoromorpholine derivatives such as 4-(trifluoromethyl) perfluoromorpholine sold under the name "PF 5052®" by the company 3M;

silicone oils such as volatile or non-volatile polymethylsiloxanes (PDMS) containing a substantially linear or cyclic silicone chain which are liquid or pasty at room temperature, in particular cyclopolydimethylsiloxanes (cyclomethicones) such as cyclohexadimethylsiloxane and cyclopentadimethylsiloxane; polydimethylsiloxanes containing alkyl, alkoxy or phenyl groups, which are pendent or at the silicone chain end, groups having from 2 to 24 carbon atoms; phenylated silicones such as phenyltrimethicones, phenyldimethicones, phenyltrimethylsiloxydiphenylsiloxanes, diphenyldimethicones, diphenylmethyldiphenyltrisiloxanes, (2-phenylethyl)trimethylsiloxysilicates and polymethylphenylsiloxanes;

mixtures thereof.

The expression "hydrocarbon oil" is understood to mean, in the list of oils cited above, any oil containing predominantly carbon and hydrogen atoms, and optionally ester, ether, fluorinated, carboxylic acid and/or alcohol groups.

The other fatty substances which may be present in the oily phase are for example fatty acids containing from 8 to 30 carbon atoms, such as stearic acid, lauric acid, palmitic acid and oleic acid; waxes such as lanolin, beeswax, carnauba or candelilla, paraffin or lignite waxes or microcrystalline waxes, ceresin or ozokerite, synthetic waxes such as polyethylene waxes, Fischer-Tropsch waxes, petroleum jelly paste; gums such as silicone gums (dimethiconol); silicone resins such as trifluoromethyl(C1–4)alkyldimethicone and trifluoropropyldimethicone.

These fatty substances may be chosen in a variety of ways by persons skilled in the art in order to prepare a composition having the desired properties, for example of consistency or of texture.

According to a preferred embodiment of the invention, the composition of the invention contains at least one silicone oil, preferably a volatile silicone oil, which may be chosen for example from cyclic or substantially linear polydimethylsiloxanes, and mixtures thereof. The cyclic polydimethylsiloxanes or cyclomethicones contain from about 3 to 9 silicon atoms, preferably from 4 to 6 silicon atoms, and may be for example cyclohexadimethylsiloxane and cyclopentadimethylsiloxane. The volatile substantially linear polydimethylsiloxanes preferably contain from about 3 to 9 silicon atoms. The volatile substantially linear polydimethylsiloxanes generally have a viscosity at 25° C. of less than or equal to 5 cSt while the cyclomethicones generally have a viscosity at 25° C. of less than or equal to 10 cSt.

The compositions of the invention may contain one or more customary adjuvants in the cosmetic and dermatological fields, hydrophilic or lipophilic gelling and/or thickening agents; moisturizing agents; emollients; hydrophilic or lipophilic active agents; anti-free radical agents; sequestrants; antioxidants; preservatives; basifying or acidifying agents; perfumes; film-forming agents; colouring matter (pigments such as iron oxides and titanium dioxide), pearlescent agents, soluble colorants), inorganic fillers; and mixtures thereof.

Suitable hydrophilic gelling agents other than the above described polymers include, for example, carboxyvinyl polymers such as carbopols (carbomers) and Pemulens (acrylate/$C_{10}$–$C_{30}$-alkylacrylate copolymer); polyacrylamides such as, for example, the crosslinked copolymers sold under the names Sepigel 305 (CTFA name: polyacrylamide/C13–C14 isoparaffin/Laureth 7) or Simulgel 600 (CTFA name: acrylamide/sodium acryloyldimethyltaurate copolymer/isohexadecane/polysorbate 80) by the company SEPPIC; cellulose derivatives such as hydroxyethylcellulose; polysaccharides and especially gums such as xanthan gum; and mixtures thereof.

Suitable lipophilic gelling agents include, for example, modified clays such as hectorite and its derivatives, for instance the products sold under the name Bentone.

The quantities of these various adjuvants are those conventionally used in the fields considered. In particular, the quantities of active agents vary according to the desired aim and are those conventionally used in the fields considered, and are for example from 0.1 to 20%, preferably from 0.5 to 10% of the total weight of the composition.

Active Agents

As indicated above, the composition of the invention is stable in the presence of oxidation-sensitive hydrophilic active agents and makes it possible to stabilize such active agents. According to the invention, the expression "hydrophilic active agent" is understood to mean a compound having a solubility in water of at least 0.25% at room temperature (25° C.). In addition, according to the invention, the expression "oxidation-sensitive hydrophilic active agent" is understood to mean any active agent of natural or synthetic origin capable of undergoing degradation by an oxidation mechanism. This oxidation phenomenon may have several causes, in particular the presence of oxygen, of light, of metal ions, a high temperature, or alternatively certain pH conditions.

Non-limiting examples of oxidation-sensitive hydrophilic active agent include ascorbic acid and its derivatives such as 5,6-di-O-dimethylsilyl ascorbate (sold by the company Exsymol under the reference PRO-AA), the potassium salt of dl-alpha-tocopheryl-21-ascorbyl phosphate (sold by the company Senju Pharmaceutical under the reference SEPIVITAL EPC), magnesium ascorbyl phosphate, sodium ascorbyl phosphate (sold by the company Roche under the reference Stay-C 50); phloroglucinol; enzymes; and mixtures thereof. Among the oxidation-sensitive hydrophilic active agents, ascorbic acid is used according to a preferred embodiment of the invention. The ascorbic acid may be of any type. Thus, it may be of natural origin, in powdered form or in the form of preferably concentrated orange juice. It may also be of synthetic origin, preferably in powdered form.

Other suitable active agents which may be used in the composition of the invention include, for example, moisturizing agents such as protein hydrolysates and polyols such as glycerine, glycols such as polyethylene glycols, and sugar derivatives; natural extracts; anti-inflammatory agents; procyannidolic oligomers; vitamins such as vitamin A (retinol), vitamin E (tocopherol), vitamin B5 (panthenol), vitamin B3 (niacinamide), derivatives of these vitamins (in particular esters) and mixtures thereof; urea; caffeine; depigmenting agents such as kojic acid, hydroquinone and caffeic acid; salicylic acid and its derivatives; alpha-hydroxy acids such as lactic acid and glycolic acid and derivatives thereof; retinoids such as carotenoids and derivatives of vitamin A; sunscreens; hydrocortisone; melatonin; extracts of algae, fungi, plants, yeasts or bacteria; steroids; anti-bacterial active agents such as 2,4,4'-trichloro-2'-hydroxydiphenyl ether (or triclosan), 3,4,4'-trichlorocarbanilide (or triclocarban) and the acids indicated above and in particular salicylic acid and its derivatives; mattifying agents such as fibres; tightening agents; and mixtures thereof.

Suitable steroids include, for example, dehydroepiandrosterone (DHEA), and (1) its precursors and biological derivatives, in particular the salts and esters of DHEA, such as DHEA sulphate and salicylate, 7-hydroxy-DHEA, 7-keto-DHEA, esters of 7-hydroxy- and 7-keto-DHEA, in particular 3-beta-acetoxy-7-oxo-DHEA, and (2) its chemical precursors and derivatives, in particular sapogenins such as diosgenin or hecogenin, and/or derivatives thereof such as hecogenin acetate, and/or natural extracts containing them and in particular extracts of Dioscorea, such as wild yam.

Suitable sunscreens (or UV-screening agents) may be chosen from organic screening agents, physical screening agents and mixtures thereof.

Suitable chemical sunscreens which may be used in the composition of the invention include any UVA and UVB screening agents which may be used in the cosmetic field.

Suitable UVB-screening agents include, for example:
(1) salicylic acid derivatives, in particular homomenthyl salicylate and octyl salicylate;
(2) cinnamic acid derivatives, in particular 2-ethylhexyl p-methoxycinnamate, marketed by the company Givaudan under the name Parsol MCX;
(3) liquid β,β-diphenylacrylate derivatives, in particular Octocrylene (2-ethylhexyl α-cyano-β,β-diphenylacrylate) marketed by the company BASF under the name UVINUL N539; and Etocrylene, sold in particular under the trade name "UVINUL N35" by BASF;
(4) p-aminobenzoic acid derivatives such as Ethylhexyl Dimethyl PABA sold in particular under the name "ESCALOL 507" by ISP, Glyceryl PABA, and PEG-25 PABA sold under the name "UVINUL P25" by BASF;
(5) 4-methylbenzylidenecamphor marketed by the company Merck under the name EUSOLEX 6300;
(6) 2-phenylbenzimidazole-5-sulphonic acid marketed under the name EUSOLEX 232 by the company Merck;
(7) 1,3,5-triazine derivatives, in particular:
2,4,6-tris[p-(2'-ethylhexyl-1'-oxycarbonyl)anilino]-1,3,5-triazine marketed by the company BASF under the name UVINUL T150, and
dioctylbutamidotriazone marketed by the company Sigma 3V under the name UVASORB HEB;
(8) mixtures of these screening agents.

Suitable UVA-screening agents include, for example:
(1) dibenzoylmethane derivatives, in particular 4-(tert-butyl)-4'-methoxydibenzoylmethane marketed by the company Givaudan under the name PARSOL 1789;
(2) 1,4-benzene[di(3-methyliden-10-camphorsulphonic)] acid optionally in partially or completely neutralized form, marketed under the name MEXORYL SX by the company Chimex;
(3) benzophenone derivatives, for example:
2,4-dihydroxybenzophenone (benzophenone-1);
2,2',4,4'-tetrahydroxybenzophenone (benzophenone-2);
2-hydroxy-4-methoxybenzophenone (benzophenone-3), marketed under the name UVINUL M40 by the company BASF;
2-hydroxy-4-methoxybenzophenone-5-sulphonic acid (benzophenone-4) and its sulphonate form (benzophenone-5), marketed by the company BASF under the name UVINUL MS40;
2,2'-dihydroxy-4,4'-dimethoxybenzophenone (benzophenone-6);
5-chloro-2-hydroxybenzophenone (benzophenone-7);
2,2'-dihydroxy-4-methoxybenzophenone (benzophenone-8);
the disodium salt of 2,2'-dihydroxy-4,4'-dimethoxybenzophenone-5,5'-disulphonic diacid (benzophenone-9);

2-hydroxy-4-methoxy-4'-methylbenzophenone (benzophenone-10);
benzophenone-11;
2-hydroxy-4-(octyloxy)benzophenone (benzophenone-12);
(4) silane derivatives or polyorganosiloxanes having benzophenone groups;
(5) anthranilates, in particular menthyl anthranilate marketed by the company Haarman & Reiner under the name NEO HELIOPAN MA;
(6) compounds containing, per molecule, at least two benzoazolyl groups or at least one benzodiazolyl group, in particular 1,4-bis-benzimidazolyl-phenylene-3,3',5,5'-tetrasulphonic acid, and its salts, marketed by the company Haarman & Reimer;
(7) silicon-containing derivatives of N-substituted benzimidazolyl-benzazoles or of benzofuranyl-benzazoles, and in particular:
2-[1-[3-[1,3,3,3-tetramethyl-1-[(trimethylsilyl)oxy]-disiloxanyl]propyl]-1H-benzimidazol-2-yl]benzoxazole;
2-[1-[3-[1,3,3,3-tetramethyl-1-[(trimethylsilyl)oxy]-disiloxanyl]propyl]-1H-benzimidazol-2-yl]benzothiazole;
2-[1-(3-trimethylsilanylpropyl)-1H-benzimidazol-2-yl]benzoxazole;
6-methoxy-1,1'-bis(3-trimethylsilanylpropyl)-1H,1'H-[2,2']dibenzimidazolylbenzoxazole;
2-[1-(3-trimethylsilanylpropyl)-1H-benzimidazol-2-yl]benzothiazole;

which are described in patent application EP-A-1 028 120;
(8) triazine derivatives, and in particular 2,4-bis{[4-(2-ethylhexyloxy)-2-hydroxy]phenyl}-6-(4-methoxy-phenyl)-1,3,5-triazine marketed by the company Ciba Geigy under the name TINOSORB S, and 2,2'-methylenebis-[6-(2H-benzotriazol-2-yl)-4-(1,1,3,3-tetramethylbutyl)-phenol] marketed by the company Ciba Geigy under the name TINOSORB M;
(9) and mixtures thereof.

It is also possible to use a mixture of several of these screening agents and a mixture of UVB-screening agents and UVA-screening agents and also mixtures with physical screening agents.

Suitable physical screening agents include, for example, titanium oxide (amorphous or crystalline titanium dioxide in rutile and/or anatase form), zinc oxide, iron oxide, zirconium oxide or cerium oxide, or mixtures thereof. These metal oxides may be in the form of particles having a micrometer or nanometer size (nanopigments). In the form of nanopigments, the average sizes of the particles range for example from 5 to 100 nm.

Moreover, at least one inorganic filler may be introduced into the composition according to the invention, in particular when the composition contains at least one organic powder, in order to obtain a composition which is particularly convenient during application to the skin, that is, a composition which is at once soft, smooth, emollient and moisturizing.

Inorganic Fillers

The inorganic fillers which may be used in the composition of the invention are highly varied. Suitable fillers include, for example, talc; kaolin; boron nitride; metal oxides (which are also present in the physical screening agents described above); micas; pearlescent agents; silica (or silicon dioxide) powders; bismuth oxychloride; zinc stearate; particles of alkali or alkaline-earth metal salts such as particles of calcium carbonate, of barium sulphate, of calcium sulphate; platinum particles; aluminas (in particular active aluminas); aluminosilicates (in particular clays); mixed silicates of alkali and/or alkaline-earth metals (smectites, Laponites, in particular LAPONITES DS, D, XLS or XLG marketed by the company LAPORTE Industries, Ltd.); zeolites; magnesia; composite materials based on inorganic fillers; and mixtures thereof.

Suitable metal oxides include, for example, titanium oxide (amorphous or crystalline titanium dioxide in rutile and/or anatase form), zinc oxide, iron oxide, zirconium oxide or cerium oxide or mixtures thereof. These metal oxides may be in the form of particles having a micrometer or nanometer size having a mean particle size ranging for example from 5 to 100 nm. These metal oxides may be coated, preferably with a hydrophobic coating. The coated metal oxides which may be used in the composition according to the invention may, for example, have undergone one or more treatments with one or more compounds chosen from alumina, silica, aluminium derivatives (for example stearate and laurate), silicon compounds (for example silicones, polydimethylsiloxanes, alkoxysilanes, siloxysilicates), sodium compounds, iron oxides, iron esters (for example stearate), fatty acids, fatty alcohols and derivatives thereof (such as stearic acid, hydroxystearic acid, stearyl alcohol, hydroxystearyl alcohol, lauric acid and derivatives thereof), lecithin, waxes (for example carnauba wax), (meth)acrylic polymers (for example polymethyl methacrylates), fluorinated compounds (for example perfluoroalkyl compounds and perfluoroalkyl ethers). The oxides may also be treated with a mixture of these compounds or they may comprise several successive coatings.

Pearlescent agents may also be used. The expression pearlescent agents should be understood to mean iridescent particles which reflect light. Suitable pearlescent agents include, for example, natural pearl, mica coated with titanium oxide, with iron oxide, with aluminium hydroxide, with magnesium hydroxide, with silica, with a natural pigment and with bismuth oxychloride, and coloured mica-titanium, and mixtures thereof.

The silica which may be used as inorganic filler is preferably chosen from silica microspheres, such as those marketed under the name SUNSPHERE H-51 by the company Asahi Glass, or under the name Silica Beads by the company MAPRECOS.

It is also possible to use the hydrophilic or hydrophobic silicas such as those marketed by the company Degussa-Hüls under the names AEROSIL 90, AEROSIL 130, AEROSIL 150, AEROSIL 200, AEROSIL 300, AEROSIL 380, AEROSIL OX 50, SILICE FK 320 DS, AEROSIL R202, AEROSIL R805, AEROSIL R812, AEROSIL R972, AEROSIL R974.

It is also possible to use silica in aqueous dispersion, for example a dispersion of colloidal silica, such as the product marketed under the name BINDZIL 30/220® by the company Eka Chemicals, a colloidal dispersion of amorphous silica (size: 14 nanometres) in water (30/70), or the product marketed under the name COSMO S-40 by the company Catalysts Chemicals (size: 18 nanometres).

The silica may also consist of a particle completely or partially coated with silica, for example, an inorganic particle completely or partially coated with silica, such as silica beads containing titanium oxide, marketed under the name TORAYCERAM S-IT® by the company Toray; silica-alumina microspheres containing titanium oxide (size: 105 µm), marketed under the name Z-LIGHT-SPHERE W 1012® by the company Zeelan; particles of amorphous precipitated synthetic silica/titanium oxide (size: 106–500 µm), marketed under the name NEOSIL PC20S® by the company Crosfield; Nylon-6-silica-titanium oxide fibres (length of 2 mm and thickness of 2 deniers), marketed under the name FIBERLON Y2® by the company Wackherr; silica coated with titanium dioxide and coated with porous silica (85/5/10) (size: 0.6 µm), marketed under the name ACS-0050510® by the company SACI-CFPA; anatase nanotitanium oxide treated with alumina and silica at 40% in water (size: 60 nm, monodisperse), marketed under the name MIRASUN TIW 60® by the company Rhodia Chimie CRA; anatase nanotitanium oxide (60 nm) coated with silica/alumina/cerium IV 15/5/3 in aqueous dispersion at 32%, marketed under the name MIRASUN TIW 160® by the company Rhodia Chimie CRA; anatase nanotitanium oxide treated with alumina and silica (34/4.3/1.7) in aqueous dispersion at 40%, marketed under the name TIOVEIL AQ-N® by the company Uniqema; nanotitanium oxide coated with silica (66/33) (particle size of the titanium dioxide: 30 nm; thickness of silica: 4 nm), marketed under the name MAXLIGHT TS-04® by the company Nichimen Europe PLC; and nanotitanium oxide coated with silica (80/20) (particle size of titanium dioxide: 30 nm; thickness of silica: 2 nm) marketed under the name MAXLIGHT TS-042® by the company Nichimen Europe PLC. These particles may also have optical properties in the composition such as on the skin.

The inorganic filler may be introduced into the composition after mixing the other constituents. For example, in the case of an emulsion, it may be introduced after preparing the emulsion, or alternatively if an oily phase is present, into the oily phase of the composition.

The inorganic fillers which may be used in the composition in accordance with the invention are preferably present in quantities, as active material, ranging from 0.05 to 30% by weight, more preferably from 0.1 to 20% by weight, and most preferably from 0.5 to 10% by weight relative to the total weight of the composition.

Of course, persons skilled in the art will be careful to choose the possible adjuvant(s) added to the composition according to the invention such that the advantageous properties intrinsically attached to the composition in accordance with the invention are not, or not substantially, impaired by the addition envisaged.

The composition preferably has a pH which does not overly irritate the skin, and which preferably ranges from 3 to 8, most preferably from 4.5 to 7.

The compositions of the invention may be used as a care (or treatment), protective, cleansing, make-up and/or make-up-removing product for keratin materials (skin, hair, scalp, eyelashes, eyebrows, nails or mucous membranes), such as protective, treatment or care creams for the face, for the hands or for the body, protective or care body milks, gels or foams for the care of the skin and/or of the mucous membranes (lips).

The compositions of the invention containing sunscreens may also be used as sun protection product.

The compositions of the invention may also be used as make-up products, in particular make-up products for the skin, the eyebrows, the eyelashes and the lips. The make-up products are most often coloured and generally contain pigments. In the form of make-up products, the compositions according to the invention may advantageously constitute a foundation, a lipstick, a blusher, an eyeshadow, a mascara or an eyeliner.

The compositions according to the invention may also be used as rinse-out products or leave-in products for cleansing the skin of the face and/or of the body and/or for cleansing the hair, for example as hair products, including for hair care and conditioning.

According to one aspect of the invention, the cosmetic use of a cosmetic composition as defined above, as care, cleansing and/or make-up-removing product for the skin, the hair, the scalp, the eyelashes, the eyebrows, the nails or the mucous membranes is provided.

Another aspect of the invention is the cosmetic use of a cosmetic composition as defined above, as a make-up product.

Yet another aspect of the invention is the cosmetic use of a cosmetic composition as defined above, as sun protection product (protection against sunlight and/or the UV radiation from tanning equipment).

Another aspect of the invention is the cosmetic use of a cosmetic composition as defined above, as a rinse-out or leave-in hair product.

Yet another aspect of the invention is a method for the cosmetic (non-therapeutic) treatment of a keratin material (skin, scalp, hair, eyelashes, eyebrows, nails or mucous membranes), wherein cosmetic composition as defined above is applied to the keratin material. The keratin material is preferably the skin.

The examples which follow will make it possible to understand the invention more clearly, without however being of a limiting nature. The quantities indicated are in % by weight, unless otherwise stated.

EXAMPLE 1 ACCORDING TO THE INVENTION

Gel

| | |
|---|---|
| Ammonium polyacryldimethyltauramide (Hostacerin AMPS from the company Clariant) | 1% |
| Preservative | qs% |
| HMW2220 (Dow Corning) | 2% |
| Water | qs 100% |

Procedure: The AMPS gel is prepared with the use of heat, with stirring. The mixture is cooled and then the HMW2220 dispersion is added with low shearing of the dispersion.

A translucent gel is obtained which is very light, smooth and fresh on application without a greasy feel.

COMPARATIVE EXAMPLE 1

Gel

| | |
|---|---|
| Sodium carbomer (gelling agent) | 1% |
| Preservative | qs % |
| HMW2220 (Dow Corning) (aqueous dispersion at 60% of A.M.) (that is, 1.2% of A.M.) | 2% |
| Water | qs 100% |

Procedure: The carbomer gel is prepared with the use of heat, with stirring. The mixture is cooled and then the HMW2220 dispersion is added with low shearing of the dispersion.

A white to translucent gel is obtained which is smooth on application but sticky during application and which leaves a sticky appearance after application.

EXAMPLE 2 ACCORDING TO THE INVENTION

O/W Emulsion

| Phase A (oily phase) | |
| --- | --- |
| Mixture of cocoyl ethylglucoside and of cetyl stearyl alcohol (35/65) (Montanov 82 from the company SEPPIC) | 3% |
| Apricot oil | 10% |
| Cyclohexadimethylsiloxane | 5% |
| Petroleum jelly paste | 10% |
| Stearic acid | 0.5% |
| Phase B (aqueous phase) | |
| Glycerine | 5% |
| Acrylamide/sodium acrylamido-2-methylpropane-sulphonate copolymer in inverse emulsion at 40% in polysorbate (Simulgel 600 from the company Seppic) | 1% |
| Preservative | qs % |
| Water | qs 100% |
| Phase C | |
| HMW2220 (Dow Corning) (aqueous dispersion at 60% of A.M.) (that is, 1.2% of A.M.) | 2% |
| Perfume | 0.1% |

Procedure: Phase B is prepared with the use of heat, with stirring. Phase A is added thereto. The mixture is cooled and then phase C is added with low shearing of the dispersion.

A white cream is obtained which is very smooth on application with no greasy or sticky feel, giving a good moisturizing sensation after application.

EXAMPLE 3 ACCORDING TO THE INVENTION

Foundation (O/W)

| Phase A (oily phase) | |
| --- | --- |
| Cyclopentadimethylsiloxane | 4% |
| Cyclohexadimethylsiloxane | 10% |
| Non-volatile silicone oils (polyphenylmethyl-siloxane and polycetylmethylsiloxane) | 12% |
| Polyethylene glycol stearate | 0.6% |
| Glyceryl stearate | 0.3% |
| Stearic acid | 1.9% |
| Coated yellow iron oxide | 1.6% |
| Brown iron oxide | 0.5% |
| Black iron oxide | 0.3% |
| Nylon 12 powder | 6% |
| Polyethylene powder | 4% |
| Phase B (aqueous phase) | |
| Propylene glycol | 6.5% |
| Polyethylene glycol 32 EO (PEG-32) | 10% |
| Preservative | qs |
| Ammonium polyacryldimethyltauramide (Hostacerin AMPS from the company Clariant) | 1.5% |
| Water | qs |
| Phase C | |
| HMW2220 (Dow Corning) (aqueous dispersion at 60% of A.M.) (that is, 1.2% of A.M.) | 2% |
| Perfume | 0.1% |

Procedure: The composition is prepared by heating the constituents of the oily phase A, apart from the volatile oils, to 65° C. and by mixing. The volatile oils are then added at 60° C. In parallel, the aqueous phase B is prepared at 80° C. The mixture is allowed to cool to 30° C. The two phases are mixed, with Moritz stirring, by pouring the oily phase into the aqueous phase. Next, phase C is added, with low stirring.

A smooth foundation is thus obtained. This foundation is fluid, coloured and has a very smooth texture; it spreads well and can be applied uniformly.

EXAMPLE 4 ACCORDING TO THE INVENTION

O/W Emulsion

| Phase A (oily phase) | |
| --- | --- |
| Cyclohexadimethylsiloxane | 5% |
| Isohexadecane | 5% |
| Phase B (aqueous phase) | |
| Glycerine | 4% |
| Propylene glycol | 3% |
| Arlacel 165 (glyceryl stearate/PEG-5 stearate) | 2% |
| Preservative | qs % |
| Ammonium polyacryldimethyltauramide (Hostacerin AMPS from the company Clariant) | 1% |
| Water | qs 100% |
| Phase C | |
| Modified starch (Aluminium Starch Octenyl succinate DRY FLO from the company National Starch) | 2% |
| Acrylates copolymer (Expancel 551 DE20 from the company Kemanord Plast) | 0.5% |
| Phase D | |
| HMW2220 (Dow Corning) (aqueous dispersion at 60% of A.M.) (that is, 1.2% of A.M.) | 2% |

Procedure: Phases A and B are prepared and phase A is incorporated into phase B, with stirring. Phase C is added thereto. Phase D is then added with low shearing.

A powdered white homogeneous cream is obtained which is smooth on application and easy to spread.

EXAMPLE 5 ACCORDING TO THE INVENTION

O/W Emulsion

| Phase A (oily phase) | |
| --- | --- |
| Mixture of arachidyl polyglucoside and of arachidyl and behenyl alcohols (15/85) (Montanov 202 from the company SEPPIC) | 1.5% |
| Mixture of glyceryl mono- or distearate and of potassium stearate (TEGIN from the company Goldschmidt) | 1.5% |
| Apricot oil | 5% |
| Cyclohexadimethylsiloxane | 10% |
| Phase B (aqueous phase) | |
| Glycerine | 5% |
| Ammonium polyacryldimethyltauramide (Hostacerin AMPS from the company Clariant) | 1% |

-continued

| | |
|---|---|
| Preservative | qs |
| Water | qs 100% |
| Phase C | |
| Nylon powder (ORGASOL 2002 D NAT COS) | 2% |
| Phase D | |
| HMW2220 (Dow Corning) (aqueous dispersion at 60% of A.M.) (that is, 1.2% of A.M.) | 2% |

Procedure: Phases A and B are prepared with the use of heat (about 80° C.) and phase A is incorporated into phase B, with stirring. After cooling to 40° C., phase C is added. Phase D is then added, with low shearing.

A powdered white homogeneous cream is obtained which is smooth on application and easy to spread.

EXAMPLE 6 ACCORDING TO THE INVENTION

W/O Emulsion

| | |
|---|---|
| Phase A (oily phase) | |
| Cetyl dimethicone copolyol (ABIL EM 90 from the company Goldschmidt) | 1.5% |
| Polyglyceryl isostearate (Isolan GI 34 from the company Goldschmidt) | 0.5% |
| Isohexadecane | 10% |
| Apricot oil | 5% |
| Cyclohexadimethylsiloxane | 8% |
| Acrylates copolymer (Expancel 551 DE20 from Expancel) | 0.5% |
| Polydimethylsilsesquioxane powder (Tospearl 240 from the company Toshiba) | 1% |
| Phase B (aqueous phase) | |
| Glycerine | 5% |
| Magnesium sulphate | 0.7% |
| HMW2220 (Dow Corning) (aqueous dispersion at 60% of A.M.) (that is, 1.2% of A.M.) | 2% |
| Preservative | qs |
| Water | qs 100% |

Procedure: Phases A and B are prepared at low temperature and phase B is incorporated into phase A, with stirring.

A smooth white homogeneous cream is obtained which is not greasy when applied to the skin.

EXAMPLE 7 ACCORDING TO THE INVENTION

Pearlescent Gel

| | |
|---|---|
| Phase A | |
| Glycerine | 4% |
| Propylene glycol | 3% |
| Preservative | qs % |
| Acrylamide/sodium acrylamido-2-methylpropane-sulphonate copolymer in inverse emulsion at 40% in polysorbate (Simulgel 600 from the company SEPPIC) | 1.5% |
| Methyl methacrylate/ethylene glycol dimethacrylate copolymer powder (Microspheres M305 from the company Matsumoto) | 1% |
| Mica-titanium oxide (Flamenco red 420C from the company Engelhard) | 2% |
| Water | qs 100% |
| Phase B | |
| HMW2220 (Dow Corning) (aqueous dispersion at 60% of A.M.) (that is, 1.2% of A.M.) | 2% |

Procedure: The ingredients of phase A are mixed with the use of heat, with stirring. The mixture is then cooled to 30° C. and phase B is added with low shearing.

A translucent and pearlescent gel is obtained which is very smooth to the touch and fresh during application to the skin. This gel may be used as body or face cream.

EXAMPLE 8 ACCORDING TO THE INVENTION

O/W Emulsion

| | |
|---|---|
| Phase A (oily phase) | |
| Mixture of arachidyl polyglucoside and of arachidyl and behenyl alcohols (15/85) (Montanov 202 from the company SEPPIC) | 1.5% |
| Mixture of glyceryl mono- or distearate and of potassium stearate (93/7) (TEGIN from the company Goldschmidt) | 1.5% |
| Cyclohexadimethylsiloxane | 5% |
| Phase B (aqueous phase) | |
| Glycerine | 5% |
| Preservative | qs |
| Water | qs 100% |
| Phase C | |
| Ammonium polyacryldimethyltauramide (Hostacerin AMPS) | 1% |
| Xanthan gum | 0.2% |
| Cyclohexadimethylsiloxane | 5% |
| Phase D | |
| Ascorbic acid | 5% |
| Water | 20% |
| Phase E | |
| HMW2220 (Dow Corning) (aqueous dispersion at 60% of A.M.) (that is, 1.8% of A.M.) | 3% |

Procedure: At 70–75° C., phase A is homogenized using a magnetic stirrer. At 85° C., phase B is homogenized using a magnetic stirrer. At 70–75° C., phase A is introduced into phase B, with stirring. Next, phase C is introduced into the mixture obtained. The mixing is carried out until a fine emulsion is obtained and it is cooled. At 25° C., phase D and then phase E are introduced, with gentle stirring.

A slippery white cream is obtained which is very smooth on application.

After three weeks at 50° C., the emulsion remained stable and it exhibits no phase release or separation. In addition, the variation of the colour (yellowing) is a lot less than with the prior art compositions (see comparative examples below).

COMPARATIVE EXAMPLE 2

O/W Emulsion

| Phase A (oily phase) | |
|---|---|
| Mixture of arachidyl polyglucoside and of arachidyl and behenyl alcohols (15/85) (Montanov 202 from the company SEPPIC) | 1.5% |
| Mixture of glyceryl mono- or distearate and of potassium stearate (93/7) (TEGIN from the company Goldschmidt) | 1.5% |
| Cyclohexadimethylsiloxane | 5% |
| Phase B (aqueous phase) | |
| Glycerine | 5% |
| Preservative | qs |
| Water | qs 100% |
| Phase C | |
| Ammonium polyacryldimethyltauramide (Hostacerin AMPS) | 1% |
| Xanthan gum | 0.2% |
| Cyclohexadimethylsiloxane | 5% |
| Phase D | |
| Ascorbic acid | 5% |
| Water | 20% |

Procedure: At 70–75° C., phase A is homogenized using a magnetic stirrer. At 85° C., phase B is homogenized using a magnetic stirrer. At 70–75° C., phase A is introduced into phase B, with stirring. Next, phase C is introduced into the mixture obtained. The mixing is carried out until a fine emulsion is obtained and it is cooled. At 25° C., phase D is introduced, with gentle stirring.

A slippery white cream is obtained which is rough on application.

After three weeks at 50° C., the emulsion is destabilized and there is release of oil and of water at the bottom of the pot containing the emulsion. In addition, the composition has become intensely yellow.

COMPARATIVE EXAMPLE 3

O/W Emulsion

| Phase A (oily phase) | |
|---|---|
| Mixture of arachidyl polyglucoside and of arachidyl and behenyl alcohols (15/85) (Montanov 202 from the company SEPPIC) | 1.5% |
| Mixture of glyceryl mono- or distearate and of potassium stearate (93/7) (TEGIN from the company Goldschmidt) | 1.5% |
| Cyclohexadimethylsiloxane | 3% |
| Silicone elastomer in oily dispersion (mixture of crosslinked polydimethylsiloxane and of polydimethylsiloxane (6 cst) (24/76) (KSG 16) | 3% |
| Phase B (aqueous phase) | |
| Glycerine | 5% |
| Preservative | qs |
| Water | qs 100% |
| Phase C | |
| Ammonium polyacryldimethyltauramide (Hostacerin AMPS) | 1% |
| Xanthan gum | 0.2% |
| Cyclohexadimethylsiloxane | 5% |
| Phase D | |
| Ascorbic acid | 5% |
| Water | 20% |

Procedure: At 70–75° C., phase A is homogenized using a magnetic stirrer. At 85° C., phase B is homogenized using a magnetic stirrer. At 70–75° C., phase A is introduced into phase B, with stirring. Next, phase C is introduced into the mixture obtained. The mixing is carried out until a fine emulsion is obtained and it is cooled. At 25° C., phase D is introduced, with gentle stirring.

A slippery white cream is obtained which is very smooth on application.

After three weeks at 50° C., the emulsion is destabilized and there is a very substantial release of oil and a substantial release of water at the bottom of the pot containing the emulsion. In addition, the composition has become intensely yellow.

It is evident from Example 8 according to the invention and from the Comparative Examples 2 and 3 above that the composition according to the invention containing vitamin C is a lot more stable than a composition not containing a dispersion of silicone copolymer or than a composition containing an oily dispersion of crosslinked silicone elastomer of the prior art.

EXAMPLE 10 ACCORDING TO THE INVENTION

Serum

| Ammonium polyacryldimethyltauramide (Hostacerin AMPS) | 0.8% |
|---|---|
| Sodium hyaluronate | 0.1% |
| HMW2220 (Dow Corning) (aqueous dispersion at 60% of A.M.) (that is, 3% of A.M.) | 5% |
| Covabead LH85 (Wackherr) | 2% |
| Titanium dioxide | 1% |
| Ethanol | 10% |
| Glycerine | 5% |
| Perfume | 0.5% |
| Preservative | qs % |
| Water | qs 100% |

Procedure: The AMPS and the sodium hyaluronate are dispersed, with stirring, in the aqueous phase comprising the water, the glycerine and the preservatives until complete solubilization is obtained. The HMW 2220, the Covabead LH85 and the titanium dioxide are dispersed and homogenized in the mixture previously obtained. The perfume, presolubilized in the alcohol, is then added thereto.

A serum is obtained which is fresh and smooth on application, which may be used alone or under a care product.

EXAMPLE 11 ACCORDING TO THE INVENTION

O/W Emulsion

| Phase A (oily phase) | |
|---|---|
| PEG-20 methyl glucose sesquistearate | 2% |
| Apricot oil | 4% |
| Cyclohexadimethylsiloxane | 5% |
| Cyclopentadimethylsiloxane/dimethiconol (DC2-9071 from Dow Corning) (silicone gum) | 5% |
| Vitamin E | 0.25% |
| Retinol palmitate | 0.1% |
| Phase B (aqueous phase) | |
| AMPS/sodium acrylate copolymer in inverse emulsion (SIMULGEL EG from the company SEPPIC) | 1.5% |
| Glycerine | 7% |
| Hostacerin AMPS | 0.5% |
| Preservative | qs |
| Colourant | qs |
| Water | qs 100% |
| Phase C | |
| HMW2220 (Dow Corning) (aqueous dispersion at 60% of A.M.) (that is, 1.2% of A.M.) | 2% |
| Silica (Sunsphere H51 from the company Asahi) | 8% |
| Expancel 551DE20 | 0.5% |

Procedure: Phase A is prepared by heating the constituents of this phase to 60° C. Phase B is prepared by heating the mixture of water and of glycerine to 65° C., by solubilizing preservatives and colourant therein, by adding the Hostacerin AMPS and by maintaining the stirring until gel formation is obtained. The emulsion is prepared by pouring phase A at 60° C. into phase B at 65° C., with stirring, and then the Simulgel EG is added; the mixture is homogenized and cooled to 30° C. Phase C is then added, with stirring.

A fluid is obtained as an emulsion which has a surprising effect of smoothness and comfort and which can be used in the morning and/or in the evening. This fluid was tested on a panel of 30 women who found it very smooth on application, light and comfortable, leaving the skin very soft.

EXAMPLE 12 ACCORDING TO THE INVENTION

Powdered Lotion

| | |
|---|---|
| HMW2220 (Dow Corning) (aqueous dispersion at 60% of A.M.) (that is, 1.2% of A.M.) | 2% |
| Silica (Sunsphere H51 from the company Asahi) | 5% |
| Covabead LH85 (from the company Wackherr) | 1% |
| Zinc dioxide | 1% |
| Ethanol at 96° | 15% |
| Glycerine | 3% |
| Perfume | qs % |
| Water | qs 100% |

Procedure: To the mixture of water and of glycerine, there are added, with stirring, HMW 2220, silica, Covabead LH85 and zinc dioxide, and then the mixture of perfume and of ethanol.

A matifying powdered lotion of great smoothness is obtained. This lotion is applied after stirring in order to rehomogenize it before use. It can be used in the morning and/or in the evening before applying the usual care product.

EXAMPLE 13 ACCORDING TO THE INVENTION

W/O Emulsion (Cast)

| Phase A (oily phase) | |
|---|---|
| Abil WE09 | 9% |
| Phenyltrimethicone | 5% |
| Cyclohexadimethylsiloxane | 15% |
| Polyethylene wax | 3% |
| Hydrogenated jojoba oil | 6% |
| Nylon 12 (Orgasol 2002 Extra from the company Atochem) | 3% |
| Phase B (aqueous phase) | |
| Glycerine | 7% |
| Magnesium sulphate | 1% |
| HMW2220 (Dow Corning) (aqueous dispersion at 60% of A.M.) (that is, 3% of A.M.) | 5% |
| Silica (Sunsphere H51 from the company Asahi) | 4% |
| Preservative | qs |
| Perfume | qs |
| Water | qs 100% |

Procedure: The oily phase (A) is homogenized at 95° C. in order to melt the waxes. The aqueous phase (B) is heated to 85° C. The aqueous phase is then added to the oily phase, with stirring, and the mixture is cooled to 75° C. The mixture is cast in metal dishes.

A very smooth compact moisturizing product is obtained. This product, by virtue of its "nomad product" presentation (that is to say that you can take it with you), can be used during the day when the skin is in need of it. It can be applied with the finger or with a sponge.

EXAMPLE 14 ACCORDING TO THE INVENTION

Powder

| Phase A | |
|---|---|
| Talc | 23% |
| Mica | 22% |
| Bismuth oxychloride | 8% |
| Zinc stearate | 3% |
| Nylon 12 (Orgasol 2002 Extra from the company Atochem) | 20% |
| Titanium dioxide | 2% |
| Phase B | |
| Iron oxides | 15.5% |
| Phase C (binder) | |
| Isocetyl stearate | 3.5% |
| HMW2220 (Dow Corning) (aqueous dispersion at 60% of A.M.) (that is, 1.8% of A.M.) | 3% |

Procedure: Phases A and B are mixed, and then premixed phase C is added dropwise thereto. The whole is then ground in a toothed roll mill, and then sieved. This powder is then compacted into dishes.

A very smooth compact powder is obtained which is applied with a sponge or with a brush either directly to the skin or over a foundation in order to obtain a velvety make-up.

This application claims priority from French patent application nos. 02/00097 (filed Jan. 4, 2002), 02/00099 (filed Jan. 4, 2002), 02/00096 (filed Jan. 4, 2002), 02/00095 (filed Jan. 4, 2002), and U.S. provisional application Nos. 60/356,142 (filed Feb. 14, 2002), 60/356,177 (Feb. 14, 2002), 60/355,823 (filed Feb. 13, 2002), 60/356,143 (filed Feb. 14, 2002), the entire contents of which are all incorporated herein by reference.

The invention claimed is:

1. A composition comprising, in a physiologically acceptable medium, at least one aqueous phase comprising (1) in dispersion, particles of a substantially linear block silicone copolymer; and (2) at least one polymer derived from a monomer or monomer mixture comprising at least one monomer having an ethylenic unsaturation and a sulphonic group.

2. The composition according to claim 1, wherein the silicone copolymer is present in an amount ranging from 0.01 to 15% by weight relative to the total weight of the composition.

3. The composition according to claim 1, wherein the particles of the silicone copolymer have a number-average size of less than or equal to 2 microns.

4. The composition according to claim 1, wherein the silicone copolymer is obtained by chain extension reaction, in the presence of a catalyst, from at least:
   a) one polysiloxane having at least one reactive group; and
   b) one organosilicone compound which reacts with the polysiloxane by chain extension reaction.

5. The composition according to claim 4, wherein the polysiloxane is selected from the group consisting of compounds of formula (I):

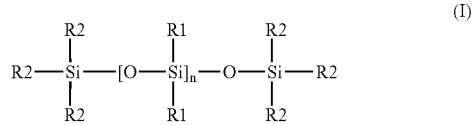

in which $R_1$ and $R_2$, independently of each other, represent a hydrocarbon group having from 1 to 20 carbon atoms, an aryl group or a reactive group, and n is an integer greater than 1, wherein there is on average between one and two reactive groups per polymer.

6. The composition according to claim 5, wherein the reactive group is selected from the group consisting of hydrogen, aliphatically unsaturated groups, hydroxyl groups, alkoxy groups, alkoxyalkoxy groups, acetoxy groups, amino groups, and mixtures thereof.

7. The composition according to claim 5, wherein $R_1$ is a methyl group.

8. The composition according to claim 5, wherein $R_2$ at the chain end represents a vinyl group.

9. The composition according to claim 4, wherein the organosilicone compound is selected from the group consisting of compounds acting as a chain extension agent and polysiloxanes of formula (I):

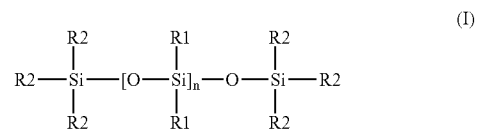

in which $R_1$ and $R_2$, independently of each other, represent a hydrocarbon group having from 1 to 20 carbon atoms, an aryl group or a reactive group, and n is an integer greater than 1, wherein there is on average between one and two reactive groups per polymer.

10. The composition according to claim 9, wherein the organosilicone compound is a liquid organohydrogenpolysiloxane of formula (II):

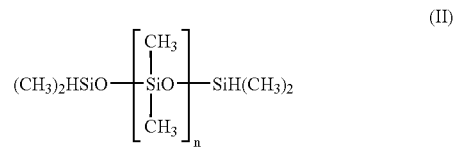

where n is an integer greater than 1.

11. The composition according to claim 10, wherein n is equal to 20.

12. The composition according to claim 4, wherein the aqueous dispersion of particles of silicone copolymer is obtained by mixing water, at least one emulsifier, the polysiloxane, the organosilicone compound and a catalyst.

13. The composition according to claim 12, wherein the dispersion is an aqueous dispersion of divinyldimethicone/dimethicone copolymer, $C_{12}$–$C_{13}$ Pareth-3 and $C_{12}$–$C_{13}$ Pareth-23.

14. The composition according to claim 1, wherein the composition comprises at least one polymer derived from a monomer or monomer mixture comprising at least one monomer having an ethylenic unsaturation and a sulphonic group and the monomer is selected from the group consisting of vinylsulphonic acid, styrenesulphonic acid, (meth)acrylamido($C_1$–$C_{22}$)alkylsulphonic acids,
   N-($C_1$–$C_{22}$)alkyl(meth)acrylamido($C_1$–$C_{22}$)alkylsulphonic acids, the partially or completely neutralized forms thereof, and mixtures thereof.

15. The composition according to claim 1, wherein the composition comprises at least one polymer derived from a monomer or monomer mixture comprising at least one monomer having an ethylenic unsaturation and a sulphonic group and the polymer is crosslinked.

16. The composition according to the claim 15, wherein crosslinking occurs using a crosslinking agent selected from the group consisting of divinylbenzene, diallyl ether, dipropylene glycol diallyl ether, polyglycol diallyl ethers, triethylene glycol divinyl ether, hydroquinone diallyl ether, ethylene glycol or tetraethylene glycol di(meth)acrylate, trimethylolpropane triacrylate, methylenebisacrylamide, methylenebismethacrylamide, triallylamine, triallyl cyanurate, diallyl maleate, tetraallylethylenediamine, tetraallyloxyethane, trimethylolpropane diallyl ether, allyl (meth)acrylate, allyl ethers of alcohols of sugars, allyl or vinyl ethers of polyfunctional alcohols, allyl esters of phosphoric and/or vinylphosphonic acid derivatives, and mixtures of these compounds.

17. The composition according to claim 16, wherein the crosslinking agent is selected from the group consisting of methylenebisacrylamide, allyl methacrylate and trimethylolpropane triacrylate (TMPTA).

18. The composition according to claim 15, wherein the degree of crosslinking ranges from 0.01 to 10 mol % relative to the polymer.

19. The composition according to claim 1, wherein the composition comprises at least one polymer derived from a monomer or monomer mixture comprising at least one monomer having an ethylenic unsaturation and a sulphonic group and the polymer is a crosslinked and neutralized homopolymer of 2-acrylamido-2-methyl-propanesulphonic acid.

20. The composition according to claim 1, wherein the composition comprises at least one polymer derived from a monomer or monomer mixture comprising at least one monomer having an ethylenic unsaturation and a sulphonic group and the polymer is an amphiphilic homopolymer which is a random amphiphilic polymer of AMPS modified by reaction with a $C_6$–$C_{22}$ mono-n-alkylamine or di-n-alkylamine.

21. The composition according to claim 1, wherein the composition comprises at least one polymer derived from a monomer or monomer mixture comprising at least one monomer having an ethylenic unsaturation and a sulphonic group and the polymer is a copolymer obtained from monomers having an ethylenic unsaturation and a sulphonic group and monomers having an ethylenic unsaturation without a sulphonic group.

22. The composition according to claim 1, wherein the composition comprises at least one polymer derived from a monomer or monomer mixture comprising at least one monomer having an ethylenic unsaturation and a sulphonic group and the polymer is an amphiphilic polymer obtained from AMPS and from at least one hydrophobic monomer having an ethylenic unsaturation containing at least one hydrophobic part having from 6 to 50 carbon atoms.

23. The composition according to claim 22, wherein the hydrophobic monomer having an ethylenic unsaturation is selected from the acrylates and the acrylamides of the following formula (III):

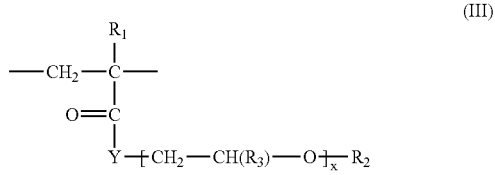

in which $R_1$ and $R_3$, which are identical or different, denote a hydrogen atom or a substantially linear or branched $C_1$–$C_6$ alkyl radical; Y denotes O or NH; $R_2$ denotes a hydrophobic hydrocarbon radical containing at least from 6 to 50 carbon atoms; and x denotes a number of moles of alkylene oxide and varies from 0 to 100.

24. The composition according to claim 23, wherein the hydrophobic radical $R_2$ is selected from the group consisting of substantially linear, branched or cyclic $C_6$–$C_{18}$ alkyl radicals; perfluorinated $C_6$–$C_{18}$ alkyl radicals; the cholesteryl radical or a cholesterol ester; and aromatic polycyclic groups.

25. The composition according to claim 23, wherein the monomer of formula (III) further comprises at least one polyoxyalkylenated chain.

26. The composition according to claim 22, wherein the amphiphilic polymer is selected from the group consisting of:
(1) copolymers containing from 15 to 60% by weight of AMPS units and from 40 to 85% by weight of ($C_8$–$C_{16}$) alkyl(meth)acrylamide units or ($C_8$–$C_{16}$)alkyl(meth) acrylate units, relative to the polymer;
(2) terpolymers containing from 10 to 90 mol % of acrylamide units, from 0.1 to 10 mol % of AMPS units and from 5 to 80 mol % of n-($C_6$–$C_{18}$)alkylacrylamide units, relative to the polymer;
(3) non-crosslinked copolymers of partially or completely neutralized AMPS and of n-dodecyl, n-hexadecyl or n-octadecyl methacrylate; and
(4) the crosslinked or non-crosslinked copolymers of partially or completely neutralized AMPS and of n-dodecylmethacrylamide.

27. The composition according to claim 22, wherein the amphiphilic polymer is selected from the copolymers is a copolymer derived from a monomer mixture comprising 2-acrylamido-2-methylpropanesulphonic acid (AMPS) units of the following formula (IV):

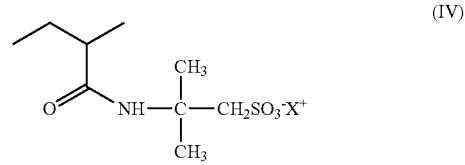

in which $X^+$ is a proton, an alkali metal cation, or the ammonium ion, and units of the following formula (V):

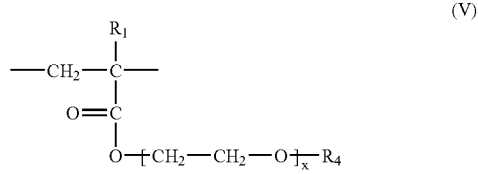

in which x denotes an integer ranging from 3 to 100; $R_1$ represents a hydrocarbon group having from 1 to 20 carbon atoms or an aryl group; and $R_4$ denotes a substantially linear or branched $C_6$–$C_{22}$.

28. The composition according to claim 1, wherein the composition comprises at least one polymer derived from a monomer or monomer mixture comprising at least one monomer having an ethylenic unsaturation and a sulphonic group and the polymer is present in an amount ranging from 0.01 to 20% by weight, relative to the total weight of the composition.

29. The composition according to claim 1, wherein the composition further comprises one or more adjuvants selected from the group consisting of gelling agents, moisturizing agents, emollients, active agents, anti-free radical agents, sequestrants, antioxidants, preservatives, basifying or acidifying agents, perfumes, film-forming agents, colouring matter, inorganic fillers, and mixtures thereof.

30. The composition according to claim 29, wherein the adjuvant is an oxidation-sensitive hydrophilic active agent selected from the group consisting of ascorbic acid, 5,6-di-O-dimethylsilyl ascorbate, the potassium salt of dl-alpha-tocopheryl-21-ascorbyl phosphate, magnesium ascorbyl phosphate, sodium ascorbyl phosphate, phloroglucinol, enzymes, and mixtures thereof.

31. The composition according to claim 29, wherein the adjuvant is an inorganic filler selected from the group consisting of talc, kaolin, boron nitride, metal oxides, micas, pearlescent agents, silica powders, bismuth oxychloride, zinc stearate, particles of alkali or alkaline-earth metal salts, platinum particles, aluminas, aluminosilicates, mixed silicates of alkali and/or alkaline-earth metals, zeolites, magnesia, composite materials based on inorganic fillers, and mixtures thereof.

32. The composition according to claim 31, wherein the inorganic filler is a metal oxide selected from the group consisting of titanium oxide, zinc oxide, iron oxide, zirconium oxide, cerium oxide, and mixtures thereof.

33. A method of protecting skin from sun comprising applying the composition of claim 29 to skin.

34. The composition according to claim 1, wherein the composition is in the form of an O/W emulsion.

35. The composition according to claim 1, wherein the composition is a cosmetic or dermatological composition.

36. The composition according to claim 1, wherein the composition constitutes a care, protective, cleansing, make-up and/or make-up-removing product for keratin materials, a sun protection product, or a hair product.

37. The composition according to claim 36, wherein the keratin material is the skin.

38. A method of caring for, cleansing and/or removing make-up from the skin, the hair, the scalp, the eyelashes, the eyebrows, the nails or the mucous membranes comprising applying the composition of claim 1 to the skin, the hair, the scalp, the eyelashes, the eyebrows, the nails or the mucous membranes.

39. A method of making-up skin comprising applying the composition of claim 1 to skin.

40. A method for the cosmetic treatment of hair comprising applying the composition of claim 1 to hair.

41. A method for the cosmetic treatment of a keratin material, comprising applying the cosmetic composition of claim 1 to the keratin material.

42. The composition according to claim 1, wherein the composition further comprises one or more organic powders.

* * * * *